US010426579B2

(12) United States Patent
Ceausu et al.

(10) Patent No.: US 10,426,579 B2
(45) Date of Patent: Oct. 1, 2019

(54) RENEWABLE DENTAL IMPLANT

(71) Applicant: Implant B Ltd., Nazareth (IL)

(72) Inventors: Liat Ceausu, Kiryat-Ono (IL); Roni Shabat, Kfar Yehezkel (IL)

(73) Assignee: IMPLANT B LTD., Nazareth (IL)

( * ) Notice: Subject to any disclaimer, the term of this patent is extended or adjusted under 35 U.S.C. 154(b) by 2 days.

(21) Appl. No.: 15/129,850

(22) PCT Filed: Mar. 26, 2015

(86) PCT No.: PCT/IL2015/050330
§ 371 (c)(1),
(2) Date: Sep. 28, 2016

(87) PCT Pub. No.: WO2015/145450
PCT Pub. Date: Oct. 1, 2015

(65) Prior Publication Data
US 2017/0165036 A1  Jun. 15, 2017

Related U.S. Application Data

(60) Provisional application No. 61/971,783, filed on Mar. 28, 2014.

(51) Int. Cl.
*A61C 8/00* (2006.01)
*A61C 8/02* (2006.01)

(52) U.S. Cl.
CPC ............ *A61C 8/0063* (2013.01); *A61C 8/006* (2013.01); *A61C 8/0006* (2013.01);
(Continued)

(58) Field of Classification Search
CPC ... A61C 8/0086; A61C 8/0063; A61C 8/0006; A61C 8/0022; A61C 8/0042;
(Continued)

(56) References Cited

U.S. PATENT DOCUMENTS 4,842,517 A * 6/1989 Kawahara ............ A61C 8/0012
433/173
4,872,840 A 10/1989 Bori
(Continued)

FOREIGN PATENT DOCUMENTS

CN    102240228       11/2011
CN    102596095 A      7/2012
(Continued)

OTHER PUBLICATIONS

International Preliminary Report on Patentability dated Oct. 13, 2016 From the International Bureau of WIPO Re. Application No. PCT/IL2015/050330.
(Continued)

*Primary Examiner* — Wade Miles
*Assistant Examiner* — Shannel N Wright
(74) *Attorney, Agent, or Firm* — Dorsey & Whitney LLP

(57) ABSTRACT

The present invention relates to an endosseous implant assembly adapted for treatment of peri-implantitis. The implant assembly comprises an implant core body configured to receive and couple with implant insert structures that potentially facilitate treatment of peri-implantitis.

20 Claims, 17 Drawing Sheets

(52) U.S. Cl.
CPC .......... *A61C 8/0015* (2013.01); *A61C 8/0022* (2013.01); *A61C 8/0042* (2013.01); *A61C 8/0045* (2013.01); *A61C 8/0074* (2013.01); *A61C 8/0075* (2013.01); *A61C 8/0089* (2013.01)

(58) Field of Classification Search
CPC ... A61C 8/0045; A61C 8/0074; A61C 8/0075; A61C 8/0018; A61C 8/0037; A61C 8/001–0012; A61C 8/0024; A61C 8/0069–0072; A61C 8/0013; A61C 2008/0046; A61C 8/0016; A61C 8/0065
See application file for complete search history.

(56) References Cited

U.S. PATENT DOCUMENTS

| | | | |
|---|---|---|---|
| 5,242,303 A | 9/1993 | De Buck | |
| 5,766,009 A | 6/1998 | Jeffcoat | |
| 5,989,027 A * | 11/1999 | Wagner | A61C 8/0006 433/173 |
| 6,095,817 A * | 8/2000 | Wagner | A61C 8/0012 433/173 |
| 6,461,160 B1 * | 10/2002 | Sutter | A61C 8/0012 433/172 |
| 8,057,230 B1 * | 11/2011 | Folsom, Jr. | A61C 8/0022 433/174 |
| 8,562,348 B2 | 10/2013 | Collins et al. | |
| 8,684,732 B2 | 4/2014 | Jacoby | |
| 9,333,054 B1 * | 5/2016 | Garfinkel | A61C 8/0009 |
| 9,901,424 B2 * | 2/2018 | Lomicka | A61C 8/0015 |
| 2003/0003128 A1 * | 1/2003 | Chiarelli | A61C 8/0012 424/423 |
| 2008/0109080 A1 * | 5/2008 | Aeschlimann | A61B 17/0401 623/16.11 |
| 2009/0011384 A1 * | 1/2009 | Collins | A61C 8/0012 433/174 |
| 2009/0036908 A1 | 2/2009 | Zokol et al. | |
| 2010/0003638 A1 * | 1/2010 | Collins | A61C 8/0012 433/174 |
| 2010/0114314 A1 | 5/2010 | Lomicka et al. | |
| 2011/0123951 A1 * | 5/2011 | Lomicka | A61C 8/0012 433/174 |
| 2011/0189634 A1 | 8/2011 | Kfir | |
| 2012/0156645 A1 * | 6/2012 | Jacoby | A61C 8/0062 433/173 |
| 2012/0156646 A1 * | 6/2012 | Pelote | A61C 8/00 433/174 |
| 2012/0225408 A1 | 9/2012 | Moore | |
| 2013/0344459 A1 * | 12/2013 | Collins | A61C 8/0012 433/174 |
| 2014/0227662 A1 * | 8/2014 | Di Girolamo | A61C 8/0071 433/174 |

FOREIGN PATENT DOCUMENTS

| | | |
|---|---|---|
| DE | 102009005573 A1 | 9/2010 |
| DE | 102009057502 | 12/2010 |
| EP | 1030622 B1 | 8/2000 |
| EP | 1030662 | 8/2000 |
| KR | 10-2011-0065380 | 6/2011 |
| TW | 201231023 A | 8/2012 |
| WO | WO 2012/165987 | 12/2012 |
| WO | WO 2013/169569 | 11/2013 |
| WO | WO 2015/145450 | 10/2015 |

OTHER PUBLICATIONS

International Search Report and the Written Opinion dated Jul. 13, 2015 From the International Searching Authority Re. Application No. PCT/IL2015/050330.

European Search Report and the European Search Opinion dated Nov. 13, 2017 From the European Patent Office Re. Application No. 15769420.9. (9 Pages).

* cited by examiner

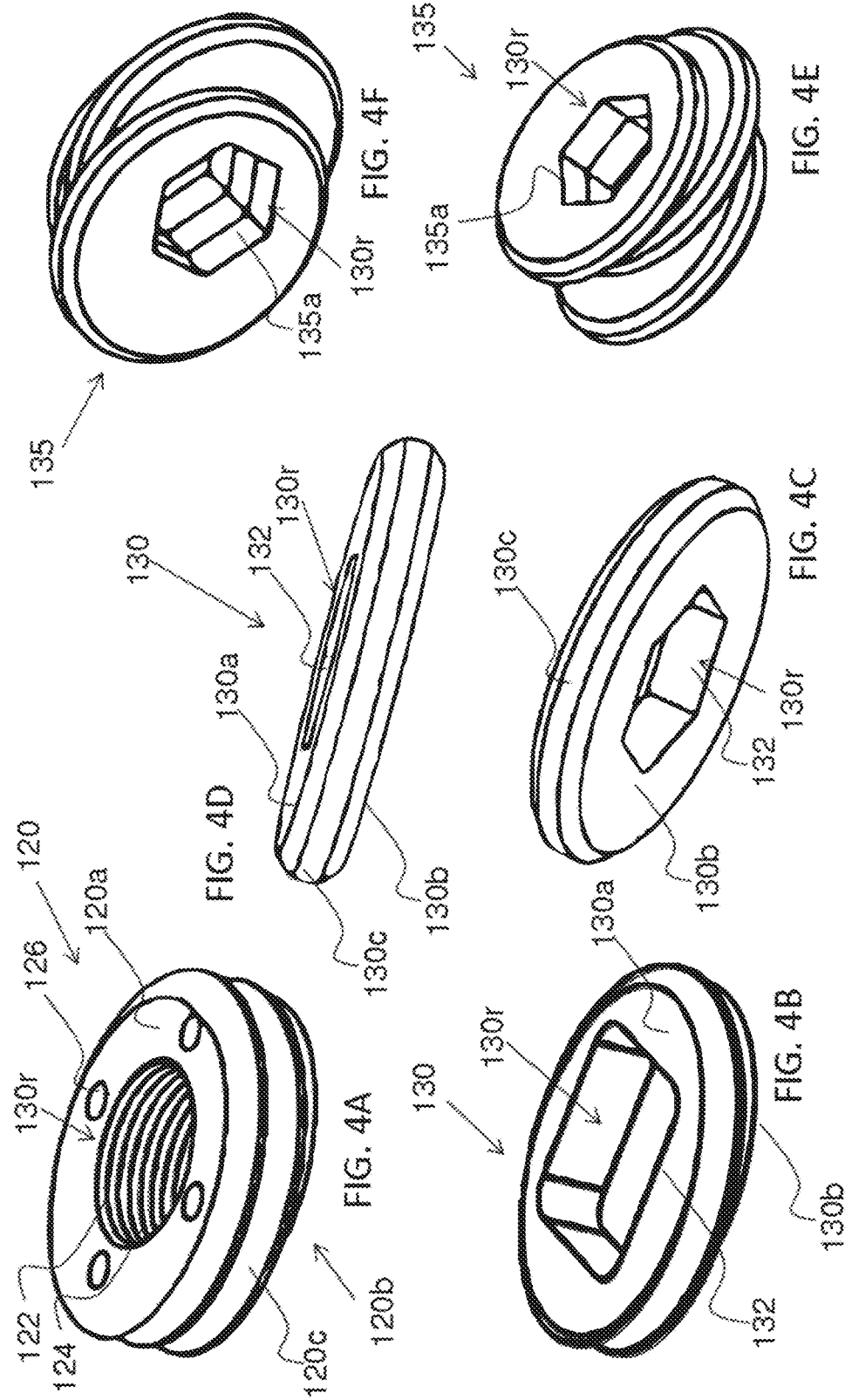

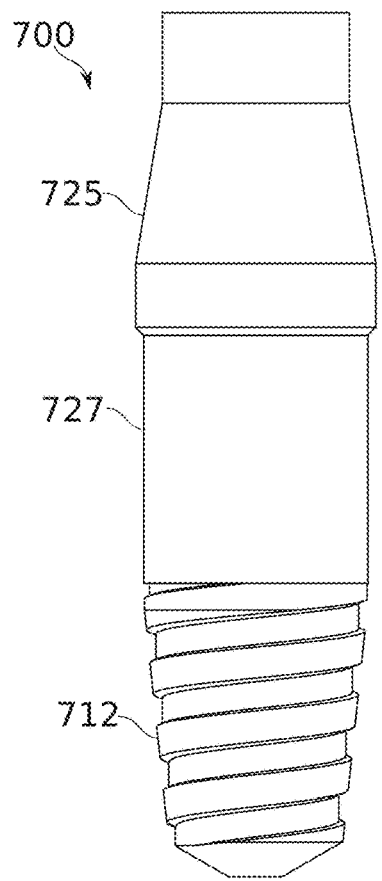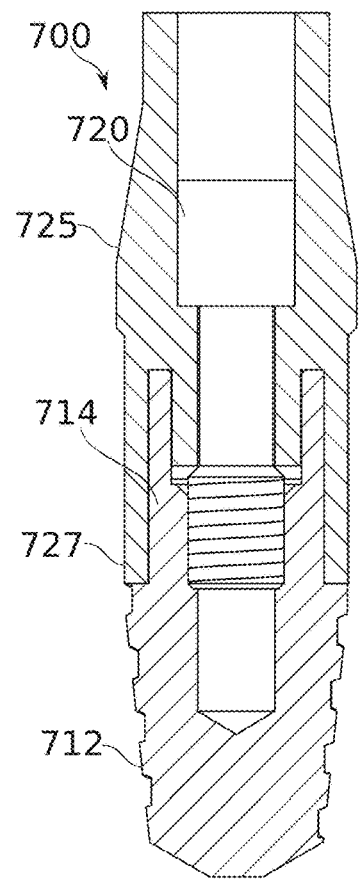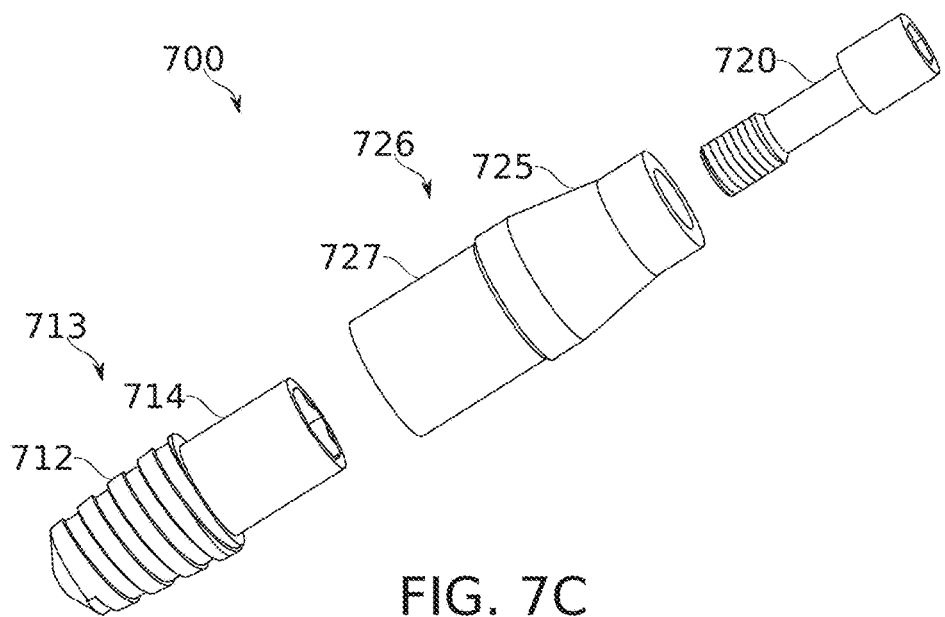

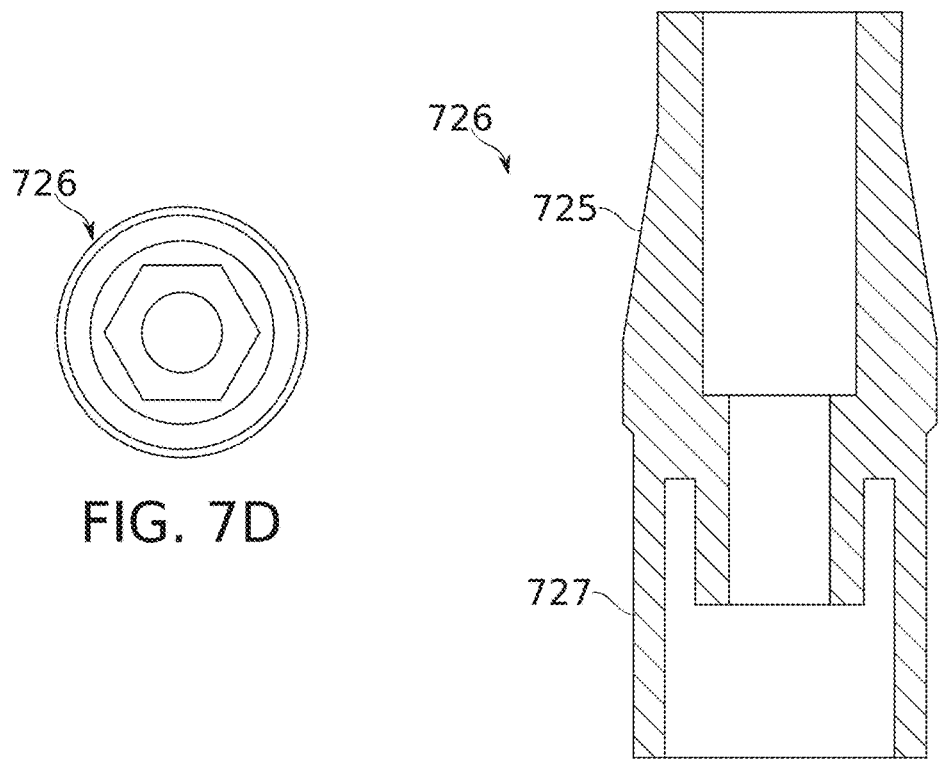
FIG. 7D
FIG. 7E
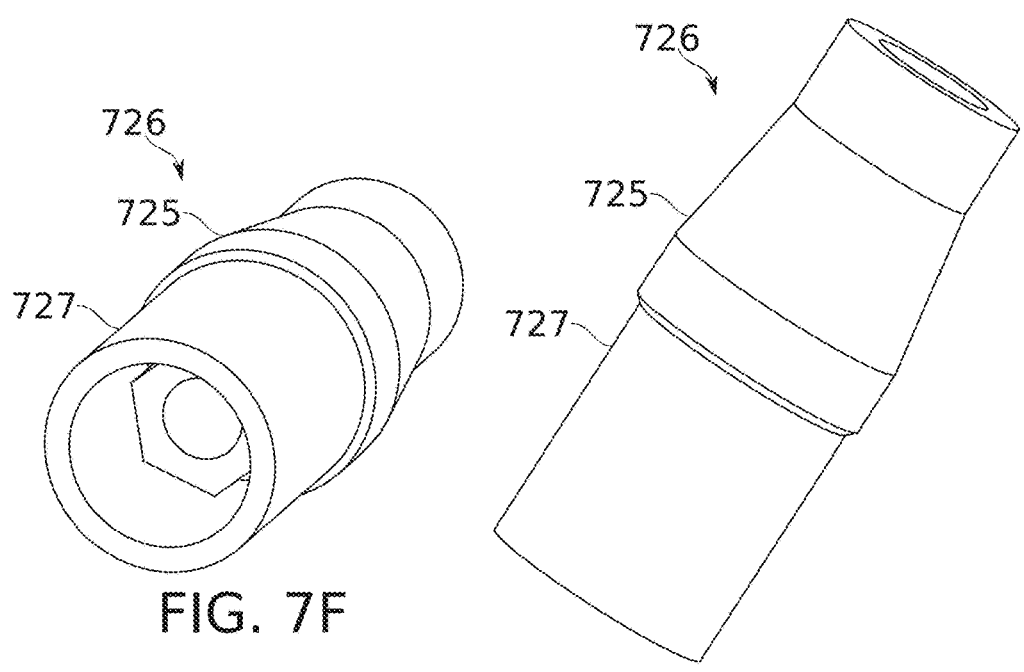
FIG. 7F
FIG. 7G

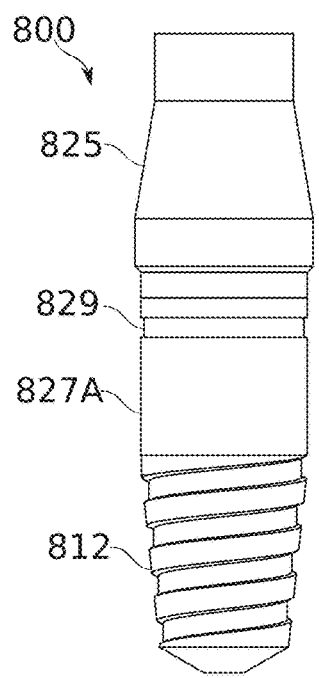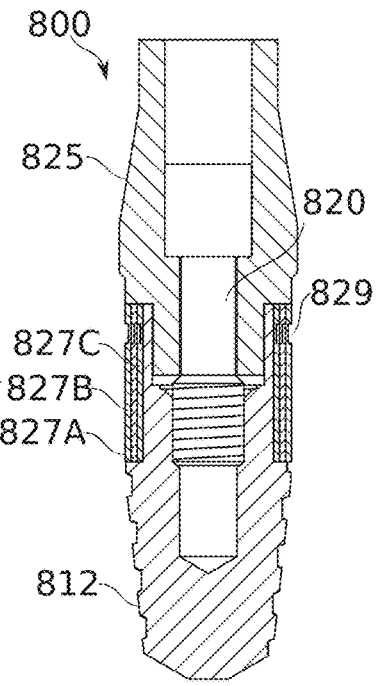
FIG. 8A          FIG. 8B
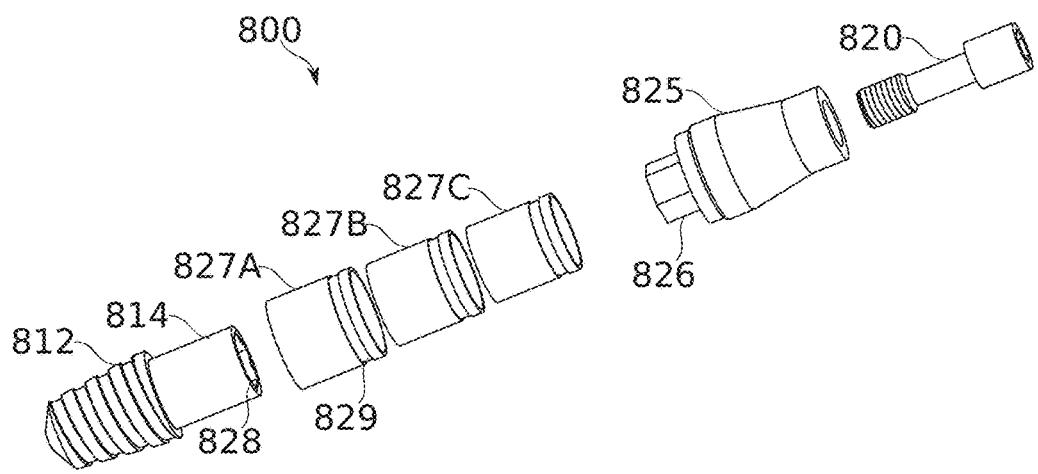
FIG. 8C

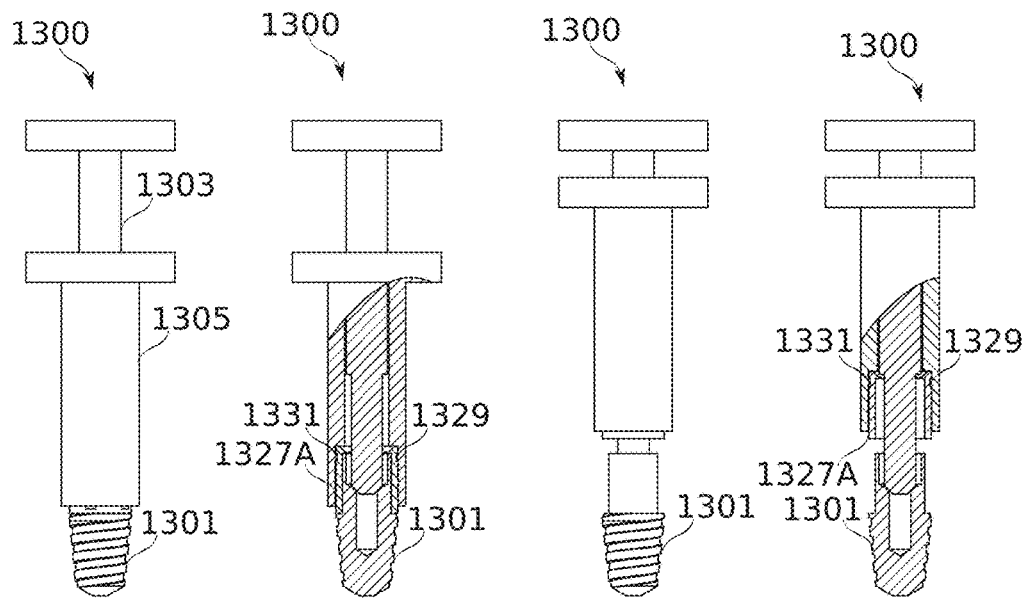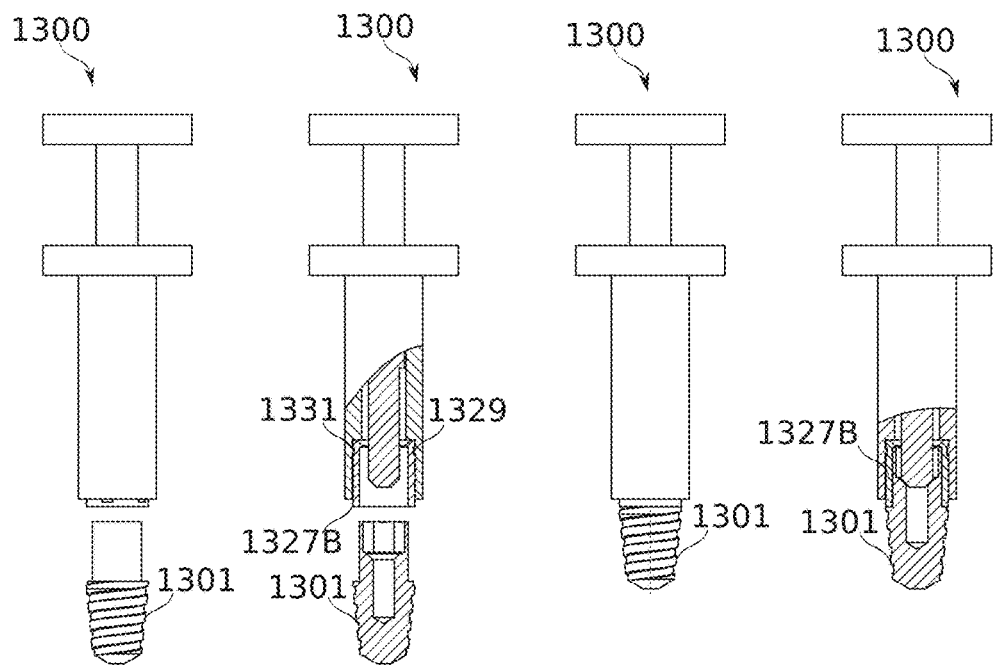

RENEWABLE DENTAL IMPLANT

RELATED APPLICATIONS

This application is a National Phase of PCT Patent Application No. PCT/IL2015/050330 having International filing date of Mar. 26, 2015, which claims the benefit of priority under 35 USC § 119(e) of U.S. Provisional Patent Application No. 61/971,783 filed on Mar. 28, 2014. The contents of the above applications are all incorporated by reference as if fully set forth herein in their entirety.

FIELD AND BACKGROUND OF THE INVENTION

The present invention, in some embodiments thereof, relates to the field of endosseous implants and more particularly, to screw form dental implant anchors for implanting within bone and adapted for treatment of peri-implantitis.

Dental implants are provided to replace lost teeth in the oral cavity. Dental implants, in conjunction with restorative complimentary parts, come together to form a structure that replaces a tooth providing both esthetic and functional purposes.

An implant-based restoration of a tooth generally includes a restoration to replace the crown portion of the lost tooth; the dental implant being provided in place of a lost tooth root. The crown and the dental implant are coupled with one another with an implant abutment. All three parts function together to bring about a successful implant-based treatment procedure. The implant serves as an anchor and provides the primary base and support structure of the dental restoration, and is therefore central to the success of the dental rehabilitation procedure.

The dental implant is generally provided as a screw-form anchor that generally includes a head portion and body portion. The head portion defines the coronal segment of the anchor that is provided for facilitating coupling with an abutment and crown. The body portion defines the apical segment of the anchor that is provided for integrating with the bone, a process known as osseointegration.

The implant body portion is generally designed according to parameters including the bone type to be implanted, and the location in which the implantation is to occur (implantation site). The body portion typically includes threading along a portion of its length that securely introduces the anchor into the bone and/or allows for the anchor to integrate with the bone.

Despite advancement in implant design, there is a continuing problem in long term implant and implant-based restoration survival. Particularly, most implants will develop peri-implantitis.

In many cases the onset and development of peri-implantitis leads to the loss, removal and eventual replacement of the entire dental implant and its attached prosthetic restoration, therein requiring a second and costly re-implantation and dental rehabilitation process.

SUMMARY OF THE INVENTION

According to an aspect of some embodiments of the present invention, there is provided a dental implant comprising: an anchor core having a base configured to anchor the core into bone, and a shaft element extending longitudinally from the base; at least one removable element having an inner surface fitted against the shaft element; wherein friction between the inner surface and the shaft element holds the removable element in a fixed location.

According to some embodiments of the invention, the friction fit is between a shaft element surface prepared to promote osseointegration, and the inner surface.

According to some embodiments of the invention, the shaft element surface has a surface geometry which promotes osseointegration.

According to some embodiments of the invention, the shaft element surface has a coating which promotes osseointegration.

According to some embodiments of the invention, the removable element is prepared to promote osseointegration.

According to some embodiments of the invention, the removable element comprises a lumen which surrounds the shaft element.

According to some embodiments of the invention, the friction fit resists movement in response to a displacement force of at least 10 Newtons applied to the removable element.

According to some embodiments of the invention, the friction between the inner surface and the shaft element is developed by a partial collapse of the inner surface onto the shaft element.

According to some embodiments of the invention, the partial collapse comprises buckling due to the exertion of longitudinal compression on the removable element.

According to some embodiments of the invention, the partial collapse comprises radial shrinkage due to the exertion of longitudinal tension on the removable element.

According to some embodiments of the invention, the partial collapse comprises radial shrinkage due to the exertion of torsion on the removable element.

According to some embodiments of the present invention, there is provided the dental implant, supplied as a kit comprising the anchor core and the at least one removable element.

According to some embodiments of the invention, the friction fit comprises a circumferential seal which prevents bacterial invasion.

According to some embodiments of the invention, the at least one removable element comprises a plurality of removable elements.

According to some embodiments of the invention, the plurality of removable elements is stacked longitudinally along the shaft element.

According to some embodiments of the invention, the plurality of removable elements are nested within each other, the outer surface of each removable element being prepared to promote osseointegration.

According to some embodiments of the invention, the removable element comprises a tubular structure having a wall thickness of less than 250 μm.

According to some embodiments of the invention, the removable element comprises a tubular structure, and the inner surface comprises a lumenal surface surrounding a lumen having a center which is radially offset from the radial center of the tubular structure.

According to some embodiments of the invention, the dental implant further comprises an abutment.

According to some embodiments of the invention, the friction held removable element is positioned proximally to an at least second removable element, and the at least second removable element is locked in position by the friction held removable element.

According to an aspect of some embodiments of the present invention, there is provided a dental implant having a renewable osseointegration surface, the dental implant comprising: a first element having a first surface prepared to promote osseointegration; and a second element having a second surface prepared to promote osseointegration; wherein the second element overlays the first surface, and the second element is separately removable from the implant to expose the first surface.

According to some embodiments of the invention, the first element is a portion of a core element, and has an extent between a proximal region of the first element adapted for abutment mounting, and a distal region, attached to a base of the core element, where in the base is adapted for securing the implant into a socket of a jaw bone.

According to some embodiments of the invention, the second element extends circumferentially around the first element.

According to some embodiments of the present invention, there is provided the dental implant, where the second element comprises a ring.

According to some embodiments of the present invention, there is provided the dental implant, where the second element comprises a wound element.

According to some embodiments of the present invention, there is provided the dental implant, where the second surface is wound to overlap itself at least once.

According to some embodiments of the present invention, there is provided the dental implant, where the second element comprises a plurality of longitudinally stacked sub-elements.

According to some embodiments of the present invention, there is provided the dental implant, where the second element comprises a plurality of separately removable sub-elements overlaying each other, each having a separate surface prepared to promote osseointegration.

According to some embodiments of the invention, the removable sub-elements comprise concentric sleeves.

According to some embodiments of the invention, a surface prepared to promote osseointegration comprises a surface which has received a surface treatment selected from the group of sandblast, sandblast large grit acid etch, titanium porous oxide, anodic oxidation, acid etching, CaP coating, titanium plasma spray, hydroxyapatite, resorbable blast media, wet shot blasting, aluminium oxide, recrystallized hydroxyapatite, beta tri-calcium phosphate coating, $TiO_2$ blast, fluoride hydrofluoric acid, hydroxyl apatite blast, sandblast large grit acid edge and NaCl solution, soluble blast media, glow discharge, titanium bead sintering, titanium-zirconium ceramic coating, titanium-niobium ceramic coating, $TiO_2$ coated, laser treatment, anodic spark deposition, plasma rich growth factors, titanium nitride coating, laser sintering, conditioning/hydroxylation, and CaP coated.

According to some embodiments of the invention, a surface prepared to promote osseointegration comprises a surface which has a geometry configured to promote osseointegration.

According to some embodiments of the invention, the geometry is configured by roughening to promote osseointegration.

According to some embodiments of the invention, the dental implant comprises the anchor core and the at least one removable element.

According to an aspect of some embodiments of the present invention, there is provided a dental implant comprising: an anchor core having a base configured to anchor the core into bone, and a shaft element extending longitudinally from the base; and at least one removable element having a receiving bore shaped to fit over the shaft element; wherein the anchor core base and shaft element are integrally formed as a monoblock, and the removable element is removable from and replaceable to the shaft element without detaching the shaft element from the anchor core.

According to some embodiments of the invention, the removable element has a wall thickness of 250 µm or less.

According to an aspect of some embodiments of the present invention, there is provided an abutment for a dental implant comprising: an upper abutment region for attachment to a dental crown or bridge, and attachable to a proximal end of a shaft element of a dental implant core; at least one sleeve element integrally formed with a distal portion of the abutment, sized with a diameter to fittingly engage the shaft element; wherein the shaft element extends longitudinally from and is thinner than a distal base of the dental implant core; and wherein the sleeve element extends along at least 30% of an intrabony region of the shaft element.

According to an aspect of some embodiments of the present invention, there is provided a dental implant comprising an anchor core having a base configured to anchor the core into bone, and a shaft element extending longitudinally from the base; and at least one removable element having an acentricly disposed lumen passing therethrough; wherein the acentricly disposed lumen is shaped to fit over the shaft element.

According to some embodiments of the invention, the dental implant comprises the anchor core and the at least one removable element.

According to some embodiments of the invention, the at least one removable element comprises a plurality of removable elements having acentricly disposed lumens at different offsets from the removable element center.

According to some embodiments of the invention, the eccentrically disposed lumen is shaped to fit over the lumen in at least two orientations distinguished by rotation of the removable element around a longitudinal axis of the shaft element.

According to some embodiments of the invention, the lumen is locked in one of the at least two orientations when fit over the shaft element.

According to some embodiments of the invention, the shaft element is acentricly disposed from a central longitudinal axis of the dental implant.

According to an aspect of some embodiments of the present invention, there is provided a dental implant comprising an anchor core having a longitudinally extending shaft element; and at least one removable element having a receiving bore fitted over the shaft element, and defined by a wall of the removable element; wherein the removable element wall is flexible to laterally expand upon receiving longitudinal compressive force, the lateral expansion remaining upon removal of the longitudinal compressive force.

According to an aspect of some embodiments of the present invention, there is provided an implant having a substantially tubular body the body comprising a distal end and a proximal end, a. the proximal end provided in the form of an abutment connection platform configured to receive an abutment; b. the substantially tubular body defining a distal portion, medial portion, and proximal portion i) the distal portion is defined adjacent to the distal end and extends proximally therefrom, the distal portion having threading the threading defining an outer diameter and an inner diameter; ii) the medial portion extending proximally from the inner core of the distal portion having a rod like body configured to have an external diameter that is iii) the proximal portion extending proximally from and continuous with the medial portion and having threading along its length.

According to some embodiments of the invention, the external diameter of the medial portion is configured to have an outer diameter that is equal to or smaller than the inner diameter of the distal portion.

According to some embodiments of the invention, the medial portion having an external surface is configured to have an anti-rotational surface cross sectional profile.

According to some embodiments of the invention, the anti-rotational surface is configured to have a cross sectional profile that is polygonal having n sides (n is larger than 2).

According to some embodiments of the invention, the anti-rotational surface is configured to have a cross sectional profile comprising a curved surface.

According to some embodiments of the invention, the anti-rotational surface is configured to have a cross sectional profile comprising a curved and a linear surface.

According to some embodiments of the invention, the medial portion surface comprises threading along at least a portion thereof.

According to some embodiments of the invention, the distal portion threading is provided in the form of self-tapping threading.

According to some embodiments of the invention, the distal portion threading comprises at least one flute.

According to some embodiments of the invention, the proximal end defines an abutment connection platform selected from the group consisting of an internal connection platform and an external abutment connection platform.

According to some embodiments of the invention, the connection platform is selected from the group consisting of an internal six receptor sockets, scalloped, internal dodecagon, external dodecagon, internal hex, external hex, external octagon, internal octagon, external spline, internal spline, morse taper, internal morse taper, one piece, internal six lobe, external six lobe, internal tri lobe, external tri-lobe, internal six spline, external six-spline, internal thread, internal pentagon, external pentagon, external thread, internal square, external square, internal five lobe, internal four lobe, internal three spline, external triangle, internal eight spline, external six lobe, internal eight lobe, internal tube to tube plug in, triangular, polygonal of n sides where n>=3 or more, any combination thereof.

According to some embodiments of the invention, the external surface of the implant is provided with a surface treatment.

According to some embodiments of the invention, the external surface of the implant is provided with a surface treatment selected from the group consisting of sandblast, SLA (Sand blast Large grit Acid etch), TPO (Titanium Porous Oxide), anodic oxidation, acid etching, CaP coating, TPS (Titanium Plasma Sprayed), HA (hydroxyapatite), machined/uncoated, RBM (Resorbable Blast Media), wet shot blasting (aluminium oxide), recrystallized hydroxyapatite, TCP (beta Tri-Calcium Phosphate coating), TiO2 blast, fluoride hydrofluoric acid, blasted with hydroxyl apatite, SLA and NaCl solution, SBM (Soluble Blast Media), texture, glow discharge, titanium bead sintering, titanium-zirconium ceramic coating, titanium-niobium ceramic coating, TiO2 coated, laser treatment, ASD (Anodic Spark Deposition), PRGF (Plasma Rich Growth Factors), titanium nitride coating, laser sintering, conditioning/hydroxylation, CaP coated, any combination thereof.

According to some embodiments of the invention, the implant body is provided from biocompatible materials.

According to some embodiments of the invention, the biocompatible materials is selected from the group consisting of commercially pure titanium (grade 1), commercially pure titanium (grade 2), commercially pure titanium (grade 3), commercially pure titanium (grade 4), titanium alloy grade 5 (Ti6Al4V), titanium alloy grade 23 (Ti6Al4V-ELI), zirconia, nTi (nano titanium) grade 4, titanium alloy grade 9 (Ti3Al2.5V), aluminium oxide (Al2O3), titanium zirconium alloy, tantalum, silver, gold, alloy, polymer, nitinol, titanium alloys, metal alloys, polymer alloys, any combination thereof.

According to an aspect of some embodiments of the present invention, there is provided an implant ring having an upper surface, a lower surface that are coupled with an external circumferential surface, having a receiving bore defined between the upper and lower surface, and wherein the external circumferential surface is a textured surface.

According to some embodiments of the invention, the external circumferential surface is provided with threading defining an outer diameter and an internal diameter.

According to some embodiments of the invention, the receiving bore comprises threading.

According to some embodiments of the invention, the receiving bore is configured to have an anti-rotational cross sectional planar profile.

According to some embodiments of the invention, the receiving bore is disposed centrically along the cross sectional plane between the upper and lower surfaces.

According to some embodiments of the invention, the receiving bore is disposed a-centrically along the cross sectional plane between the upper and lower surfaces.

According to some embodiments of the invention, the ring is coated with a coating.

According to some embodiments of the invention, the coating is provided in the form of a bone growth factor, bone growth medium, therapeutic agent, antibacterial agent, biocompatible adhesive.

According to some embodiments of the invention, at least one of the upper surface and/or lower surface and/or circumferential surfaces is provided with a surface treatment.

According to some embodiments of the invention, at least one of the upper surface and/or lower surface and/or circumferential surfaces is provided with a surface treatment selected from the group consisting of sandblast, SLA (Sand blast Large grit Acid etch), TPO (Titanium Porous Oxide), anodic oxidation, acid etching, CaP coating, TPS (Titanium Plasma Sprayed), HA (hydroxyapatite), machined/uncoated, RBM (Resorbable Blast Media), wet shot blasting (aluminium oxide), recrystallized hydroxyapatite, TCP (beta Tri-Calcium Phosphate coating), TiO2 blast, fluoride hydrofluoric acid, blasted with hydroxyl apatite, SLA and NaCl solution, SBM (Soluble Blast Media), texture, glow discharge, titanium bead sintering, titanium-zirconium ceramic coating, titanium-niobium ceramic coating, TiO2 coated, laser treatment, ASD (Anodic Spark Deposition), PRGF (Plasma Rich Growth Factors), titanium nitride coating, laser sintering, conditioning/hydroxylation, CaP coated, any combination thereof.

According to some embodiments of the invention, the implant ring further comprises a tooling recess provided along the upper surface.

According to some embodiments of the invention, the implant ring further comprises a tooling recess provided along the upper surface.

According to some embodiments of the invention, the implant rings may assume a small profile configuration having a small diameter and an expanded profile configuration having a large diameter.

According to some embodiments of the invention, a. the medial implant ring has an upper surface, a lower surface that are coupled with an external circumferential surface, and having a receiving bore defined between the upper and lower surface, the receiving bore configured and shaped according to the cross sectional profile of the implant core medial portion so as to allow stacking at least one or more medial portion ring along the length of the implant core medial portion; and b. the proximal implant ring has an upper surface, a lower surface that are coupled with an external circumferential surface, and having a receiving bore defined between the upper and lower surface, the receiving bore having threading corresponding to and configured to securely associate and lock with the threading defined along the implant core proximal portion; c. wherein the external circumferential surface is a textured surface.

According to some embodiments of the invention, the medial implant ring and the proximal implant ring have an outer diameter defined by the circumferential surface configured according to the distal portion of the implant anchor.

According to some embodiments of the invention, the assembly comprises a continuous threading pathway along the length of the external surface of the implant assembly formed along the implant anchor distal portion, the at least one medial implant ring, and the proximal implant ring.

According to an aspect of some embodiments of the present invention, there is provided a method for treating peri-implant disease the method including: a. removing a restorative structure/prosthetic members of an implant assembly; b. removing the implant abutment; c. exposing the infected implant anchor site; d. cleaning the exposed implant anchor site to removing infected tissue; e. evaluating the height of bone loss and implant anchor holding force; f. loading the implant anchor with at least one implant ring to cover at least a portion of the length of the bone loss region; g. closing the implantation site; and h. reintroducing the implant abutment and restorative structure.

According to some embodiments of the invention, the method further comprises milling/reducing at least a portion of the external surface of the implant anchor along at least a portion of the exposed bone loss region prior to loading with the at least one implant ring.

According to some embodiments of the invention, the implant is provided in the form of an implant assembly, wherein the method further comprises removing the implant rings from the infected bone loss region and loading the implant core with new implant anchor rings along the length of the bone loss region.

According to some embodiments of the invention, the method further comprises introducing a therapeutic agent within the bone loss region prior to closure of the implantation site.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 4A schematically illustrates a locking implant insert having a tooling interface disposed along an upper surface, according to some exemplary embodiments of the invention;

FIGS. 4B-4D schematically illustrate exemplary implant inserts, according to some exemplary embodiments of the invention;

FIGS. 4E-4F schematically illustrate perspective views of an acentric implant insert, according to some exemplary embodiments of the invention;

FIGS. 7A-7C schematically illustrate an implant provided with an abutment having a sleeve region which extends along a medial portion (core shaft) of the core implant body, according to some exemplary embodiments of the invention;

FIGS. 7D-7G schematically illustrate the abutment/sleeve assembly, according to some exemplary embodiments of the invention;

FIGS. 8A-8C schematically illustrate an implant comprising an insert region comprising a plurality of separately removable layers, according to some exemplary embodiments of the invention;

FIGS. 13A-13J schematically illustrate removal and/or replacement by a jacketing tool of a sleeve insert on an implant according to some exemplary embodiments of the invention.

DESCRIPTION OF SPECIFIC EMBODIMENTS OF THE INVENTION

Figure 1C:
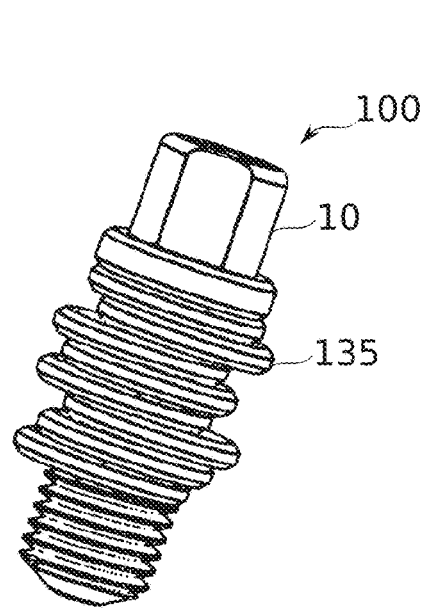
FIG. 1C schematically illustrates an assembled view of an optional implant anchor assembly comprising acentric implant inserts, according to some exemplary embodiments of the invention.

The present invention, in some embodiments thereof, relates to the field of endosseous implants and more particularly, to screw form dental implant anchors for implanting within bone and adapted for treatment of peri-implantitis.

Overview

A broad aspect of some embodiments of the current invention relates to dental implants with renewable surface capability. In some embodiments, a dental implant has portion which remains fixed within bone, and another portion which is removable and/or replaceable, and provides a portion of the outer surface of the implant when in service (that is, a surface which is in contact with tissue such as bone).

More particularly, in some embodiments of the present invention, there is provided a dental implant anchor configured to readily treat peri-implantitis without necessitating the loss of the implant and its attached restoration and/or re-implantation.

A potential advantage of having a replaceable surface part is to allow complications such as peri-implantitis to be dealt with without requiring full replacement of the implant and the prosthetic hardware it supports. For example, a dental implant surface that has become bacterially contaminated is difficult or impossible to re-condition (particularly to re-condition in place) so that it is both decontaminated, and serviceable to support osseointegration.

In some embodiments, an implant assembly comprises an implant anchor core portion adapted to receive at least one or more implant anchor rings. Optionally, the anchor rings associated with the core portion are replaced and/or interchanged in response to the development of peri-implantitis, in this way avoiding either the loss of the implant and its attached restoration or the need for re-implantation.

An aspect of some embodiments of the current invention relates to fixation of removable elements to a dental implant core by press-fitted attachment between a removable element bore and an implant core shaft.

In some embodiments of the invention, friction between a removable element and its contact surfaces is sufficient to hold the removable element in position. This provides a potential advantage by removing a requirement to "cap" (or otherwise provide an auxiliary lock to) the removable element, which potentially involves extra steps of screw threading or another locking member attachment method. An alternative potential advantage is to use a press-fit replaceable element itself as a cap, optionally to holder looser fitting elements underneath. Another alternative potential advantage is to reduce a holding requirement of a capping element; for example, the cap is optionally provided to prevent access to a bone socket environment, but is not additionally configured to exert force on elements beneath it, or is not configured to do so in a way which ensures those elements are retained. In some embodiments, the frictional holding comprises a press-fit arrangement between the removable element and a portion of the implant core to which it is fitted.

Optionally, the fit is tight enough around the core to ensure that no infection can extend along the core next to the removable element bore. Optionally, the press-fit is sufficiently strong to hold against an elastic restorative force created when the removable element is pressed down against the shaft base (the distal anchor region), so that the interface between removable element and base remains pressed shut even when insertion pressure is removed, and even if no additional capping or locking pressure is applied. In some embodiments, the development of holding force is enhanced by roughening of the core, for example, if the core is prepared for osseointegration by a surface roughening method.

Another potential advantage of a press-fit removable element is to allow greater flexibility of top-mounting prosthetic hardware. For example, abutment choice is potentially not limited by a requirement to be configured to exert force on the removable element to keep it in place.

Press-fitting to the core of the implant should be distinguished from press-fitting to the surrounding bone. Although both are potentially desirable, bone press-fitting may not be available in all situations, since the bone bore within which the removable element is mounted may be irregular and/or enlarged due to disease. Furthermore, exerting pressure on the bone potentially requires some exertion of care, since excessive pressure can lead to degeneration. Nevertheless, in some embodiments, bone-locked press-fitting also occurs.

In some embodiments, a press-fitting element is provided in a coiled configuration, the coil comprising a wound strip having an inner free end and an outer free end. Optionally, the coil comprises a cylindrical spring, the spring forces acting to counteract radial expansion of the coil. In some embodiments, the friction fitting comprises compression of the spring onto a core. Potentially, the coil winding is long enough that the potential route for infectious invasion opened by the outer free end of the coil is prevented from reaching the core. Optionally, renewal of a surface comprises removing a layer of the press-fitting element winding. Optionally, more than one layer is removed, for example, to help ensure that any potential short length harboring infectious invasion under the first winding is also removed when renewing the implant surface.

In some embodiments, establishment of press-fitting comprises deformation of a removable element due to longitudinal stresses. For example, a thin-walled removable element on a core is pressed upon so that a portion of the removable element buckles, is "squashed", or otherwise undergoes a change in radial dimensions. In some embodiments, the change comprises inward movements (radial collapsing) of the removable element wall, which thereby engages the core and locks the removable element into position. In some embodiments, friction fitting is augmented by collapsing the removable element under tension. For example, a distal end of the removable element is restrained (optionally by an insertion tool, or by spatial interference interaction with main body of the implant), and a proximal end of the removable element is pulled on, twisted, or otherwise manipulated to distort the removable element and induce friction fitting.

In some embodiments, there is a press-fitting region of surface interaction, where two surfaces interact by friction to resist translation of the outer surface over the inner surface during implant wear. For example, the friction fit is provides sufficient locking force to keep the removable element from simply falling out. More particularly, the friction fit provides sufficient locking force to prevent the removable element from working into a new position relative to the implant due to forces that the implant experiences, for example, due to bite and/or chewing forces transmitted from a crown. In some embodiments, the friction fit is of sufficient stability to allow osseointegration to establish itself upon the exposed removable element surface. In some embodiments, the friction fit resists a displacement force (along the longitudinal axis of the implant) of at least 10 N. In some embodiments, the resisted displacement force is up to at least 3-6 N, 5-10 N, 8-20 N, 15-30 N, or up to within another range of forces having the same, greater, smaller, and/or intermediate bounds.

In some embodiments, a press-fitted element comprises additional surface interaction types with the anchor core to which it fits, apart from the press-fitting friction force itself. In some embodiments, there is a region of surface interaction where two surfaces interact to provide particular resistance to bacterial or other infectious invasion. For example, an inner and outer surface meet with high tolerance (within 10 μm, 5 μm, or within another greater or lesser tolerance) at each point (or at least at points separated by no more than a minimum distance similar to that of the gap tolerance) around an extent of the circumference. The tolerance is optionally created by providing a smooth band region on each surface, the band regions being forced into apposition by tight tolerances, and/or by the expansion and/or shrinking of one or both of the surfaces. Optionally, a sealing (but not necessarily fixing) filler is placed between the surfaces. Optionally, one or both of the surfaces is tapered, to promote a tight seal upon full assembly. In some embodiments, sealing surfaces are provided at openings that provide access to the interface between anchor core and removable element, to resist infectious invasion, and potentially to ensure that when an outer surface is removed after an initial infection, the infectious agent does not remain harbored upon the newly exposed surface.

Additionally or alternatively, in some embodiments, a second surface interaction comprises a region where one surface is primarily prepared for osseointegration (for example, by a roughening and/or coating treatments), and the other surface is a covering for this surface, optionally without sealing at that region, and optionally loosely enough that there is little or no friction fitting at that region. Potentially, this helps to ensure that the surface treatment is not damaged by an overlying layer. Thus, in some embodiments, the surface interaction between removable element and core (or between two removable elements) comprises regions which press-fit to prevent movement (but optionally do not seal), regions which seal (but optionally do not promote osseointegration), and/or regions which comprise protective covering (but optionally do not seal). Optionally, the regions are provided as bands or other zones along the implant extent.

An aspect of some embodiments of the current invention relates to dental implants having a surface renewable by removal of an implant portion to expose a surface underneath the implant portion's original position.

In some embodiments, an implant comprises one or more rings or sleeves, surrounding an inner surface of an implant core (and/or another ring or sleeve). In some embodiments, an outer surface is provided by one or more strips or section; for example, a section of a ring or sleeve. Optionally, separately mounted sections are provided which together provide a circumferential surface. For example, sections are provided in longitudinal strips which individually extend along only a portion of the circumference. Optionally, separately mounted sections are separately removable. Potentially, this allows renewal of surface only in affected regions of the implant.

In some embodiments, an outer surface is provided by a strip wrapped one or more times around the implant. Optionally, exposure of the underlying surface comprises cutting away and/or unwinding of the wrapping strip. In some embodiments, separate strips overlap themselves and/or one another on only a portion of their extent. Potentially, this helps to prevent an infection from penetrating to the implant core, while still retaining separately manageable sections of the implant for surface renewal.

In some embodiments, the outermost surfaces of both removable element and the underlying removable element or core are treated to promote a particular surface-related property of the implant. In particular, the surfaces are optionally treated to promote osseointegration—for example by a coating and/or surface texturing method as known in the art.

In some embodiments, the outer removable element portion is removed as part of a procedure to control peri-implantitis. This exposes the inner surface to become the new outer surface. Potentially, the new outer surface is free of damage, residue, and/or contamination, giving renewed function to the implant surface.

In some embodiments, the renewable area of an implant is along at least 30% of the longitudinal extent of the implant which resides beyond the bone line upon implantation (the intrabony portion of the implant). In some embodiments, the renewable area is at least 50%, 70%, 90%, or another greater, lesser, or intermediate fraction of this extent. In some embodiments, the renewable area extends proximally from an anchoring region (comprising screw threads or another securing means) on the distal end of the implant. In some embodiments, the renewable area extends distally from an abutment attachment region on the proximal end of the implant. In some embodiments, the renewable region is at least 5 mm long (along the longitudinal extent of the implant). In some embodiments, the renewable region is at least 8 mm, 10 mm, 12 mm, 14 mm, or another larger, smaller, or intermediate length. In some embodiments, the renewable area of the implant fully extends around the circumference of the implant. In some embodiments, the renewable region extends around at least 95%, at least 90%, at least 70%, at least 50%, or around at least another larger, smaller, or intermediate fraction of the implant circumference.

An aspect of some embodiments of the current invention relates to a monoblock implant core having a removable and/or replaceable surface along its longitudinal extent.

In some embodiments, an implant core is formed as a single, integrally formed block. The core comprises, for example, a bone anchoring portion (which may be the distal portion of the implant), a shaft portion extending proximally from the bone anchoring portion, and a proximal attachment portion, comprising, for example, an abutment receiving surface, a bore for receiving an abutment attachment screw, and/or other structures to which additional dental implant hardware is to be attached.

In some embodiments, an implant surface along the longitudinal extent of the implant is provided by one or more sleeves, rings, or other removable elements. Optionally, the removable elements are removed, for example, upon the occurrence of an infection. Optionally, removable elements are replaceable, either after surface renewal, and/or by replacement with new removable elements.

It is a potential advantage for an implant to have a renewable surface without requiring full or partial dismantling of the portions of the implant which directly position and/or mechanically support its attached prosthetics. Since dental prosthetic parts are often functional within tight and difficult to reproduce tolerances customized to the anatomy of the patient, it is an advantage to preserve spatial relationships within the jaw to avoid the effort, expense, and/or risk of creating and implanting new parts, or attempting a refit.

By providing a removable surface, the implant can be left in place, so that the fitting of the parts which fit to it and to the rest of the mouth is not disturbed. By providing a monoblock support structure, a risk of movement of prosthetic part positioning during the replacement procedure is potentially reduced or eliminated. In particular, the monoblock design integrally couples a shaft to an anchor, leaving no possibility for relative wobble or rotation that could interfere with the tight tolerances required to replace a crown, bridge, or other mating prosthetic part. There is also a potential advantage for durability, as it avoids the production of a join region which can allow wear of parts against each other to loosen the assembled prosthetic over time.

In some embodiments, surface renewal comprises replacement of an old removable element with a new (or renewed) removable element.

An aspect of some embodiments of the current invention relates to a monoblock construction for an abutment and removable element.

In some embodiments, an abutment comprises a dental abutment, integrally formed with a sleeve that extends distally from the abutment to fit over an implant core along a substantial intrabony region of an implant core element. An intrabony region of an implant core element is a region actually or designated to reside within a bony region of a jaw—that is, surrounded on at least two sides by continuous bone, below the bone line of a mandible, and/or above the bone line of a maxilla. In some embodiments, the substantial region comprises at least 33%, 50%, 66%, or substantially all of the length between a proximal end of the implant core, and a distal widening which defines a boundary between a shaft of the implant core (along which the sleeve extends), and a distal anchoring region of the implant.

A potential advantage of this configuration is to allow a significant length of the osseointegration surface of an implant/abutment assembly to be replaceable by the exchanging of an abutment. The fixed relationship of the sleeve and abutment potentially assists the retrieval of the sleeve region, which may remain at least partially osseointegrated even when peri-implantitis has otherwise damaged the bone-implant interface. A potential advantage of the integrated form with respect to a separate piece (for example, thread-attached) construction is to remove a potential point of mechanical failure. Conversely, a potential advantage is to provide added mutual mechanical support between sleeve and abutment; for example, the abutment receives additional lateral support from the sleeve, which in turn is supported along its length by the implant core shaft.

An aspect of some embodiments of the current invention relates to a side-expanding removable element which expands laterally upon receipt of longitudinal force to engage with the sides of a surrounding bone wall.

In some embodiments, a removable element is sufficiently flexible that it displays some "spread" upon receiving longitudinal force. Potentially, the spread is retained upon release of the longitudinal force. For example, spread is at least partially inelastic, and/or locking (such as by friction along the shaft, and/or by a pressing element) prevents the spread portion from springing back to a non-spread form.

In some embodiments, a removable element is provided in a sleeve or disk form which is, initially, slightly thinner than the bone socket which has been prepared to receive it. Upon the removable element reaching the end of its travel along an implant shaft, continued pressure from above potentially induces spreading at one or more regions as the removable element compresses and/or buckles. In some embodiments, this spreading creates a contact with bone which helps to lock the removable element body in place.

An aspect of some embodiments of the current invention relates to the adjustable sizing and/or shaping of a dental implant to a bone receiving volume by selection, modification, and/or positioning of predetermined removable element portions of the dental implant. In some embodiments, a plurality of removable elements are provided along with the implant (for example, as part of a kit), to be selected among for insertion to the bone socket. Optionally, at least two removable elements are different in diameter. Optionally, at least two removable elements are different in an offset between a central receiving bore, and the outer surface of the removable element. Optionally, an offset or otherwise circularly asymmetric removable element is positionable in one of a plurality of positions (discretely or continuously defined).

A potential advantage of this configuration is to allow a degree of customizability to a removable element, for better conforming to and/or filling a bone socket space. This can be important when a bone socket space is itself circularly asymmetric, for example due to infectious bone loss. With reference to a fully customized design (that is, a removable element which is designed from scratch according to the bone socket size), there are also potential advantages. For example, a requirement to fully characterize a bone socket shape is reduced. Potentially, there are a limited number of offsets (for example, 2, 3, or 4) supported by the removable elements, and the selection of an offset is understood to involve a tolerance between removable element and bone of, for example, ±250 µm, ±400 µm, ±500 µm, ±660 µm, or another greater, lesser or intermediate tolerance due to the gaps in sizes between available options. A tolerance range for sizing is potentially acceptable, since osseointegration potentially occurs across gaps, so long as the gap is not too large. In some embodiments, moreover, a removable element is positionable in one or more of a range of insertion orientations with respect to the bone shaft.

In some embodiments, a range of positioning possibilities is increased by offsetting an implant core shaft from the central longitudinal axis of the implant anchor region. Optionally, a bore of a removable element is also acentricly disposed (herein, "acentric" means away from a central longitudinal axis; eccentric). Potentially, this allows a wider and/or more continuous range of bone socket sizes to be filled from a relatively narrow selection of implant parts, as the rotation of both the anchor in its socket and the removable element relative to the implant core both play a role in determining where a removable element is positioned.

In some embodiments, an implant anchor is adapted to have a core implant portion: a distal portion that is adapted to remain affixed within the bone; and at least one second portion, for example a medial and/or proximal portion, adaptable to facilitate treatment and/or to prevent the occurrence and/or exacerbation of peri-implantitis within the implantation site. Optionally, the core portion is sized to act as an anchor despite the development of peri-implantitis such that the core portion is defined at the distal and/or apical portion of the implant. Optionally, the adaptable portion is configured and adapted along the coronal and/or proximal portion of an implantation site where the development of peri-implantitis is common.

Optionally the ratio between core portion and adaptable portion is configured according to at least one or more parameters; for example, including but not limited to: the depth of the implantation site, implantation location, bone type, bone type distribution along the length of the implantation site, soft tissue level, the like or any combination thereof. Optionally the implant is comprises biocompatible materials selected from a group consisting of titanium, titanium alloys, Chrome-Cobalt alloy, other metal alloys, Zirconium, Hydroxyapatite coated materials, plastics, polymers, Nitinol, stainless steel, composite materials, the like or any combination thereof. Optionally the implant is manufactured with a surface treatment (for example, a treatment that roughens the surface, or, more particularly, a treatment that alters the microtopology of the surface by a method which promotes osseointegration, according to the art). Optionally the implant assumes the form of an implant selected from the group consisting of a dental implant, orthopedic implant, animal bone implant, or the like. Optionally the implant assumes a form selected from the group consisting of: trans-gingival implant, above bone implant, below bone placement implant, tissue level implant, one piece implant, multi-piece implant, bone level implant, or the like.

Within the context of this application, the terms "thread", "threading" or "threading portion" refer to a region of an element, for example, a portion of an implant, abutment, screw, sleeve, or other structure, comprising screw-type threading. Threading is used, for example, in integrating, interfacing and/or securely coupling an implant structure within the bone facilitating implantation within the bone.

Within the context of this application, the term "flute" includes reference to structures including but not limited to: vents, grooves, recesses or the like according to the art. "Flute" is used, for example, to refer to a portion of an implant provided with a cutting edge for tapping function, gathering function or the like.

Within the context of this application the term "proximal" generally refers to the side or end of an elongated medical device such as an implant that is intended to be closer to the performing medical personnel and/or practitioner. The term "proximal" may be interchangeable with the term "coronal" when referring to the coronal side of an implant. More particularly, a distal end of an implant is the end which is first inserted into bone, and resides the deepest within the bone.

Within the context of this application the term "distal" generally refers to the side or end of an elongated medical device such as an implant that is opposite the "proximal end", and is farther from the performing medical personnel and/or practitioner. The term "distal" may be interchangeable with the term "apical" when referring to the apical side of an implant.

While the following description focuses on dental implants, embodiments of the present invention are not limited to dental applications of a screw type endosseous dental implant, where embodiment of the present invention may be implemented in other skeletal bone implant applications; for example orthopedics for other regions of the body.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Embodiments of the present invention provide for device and method for the treatment of peri-implantitis by providing a dental implant assembly comprising an implant anchor core portion adapted to receive at least one or more implant anchor removable elements. The device and method of the present invention are adapted for treatment of peri-implantitis by providing for exchanging and/or replacing and/or interchanging the implant anchor removable elements associated with the anchor core in response to the development of peri-implantitis.

Figure 1A:
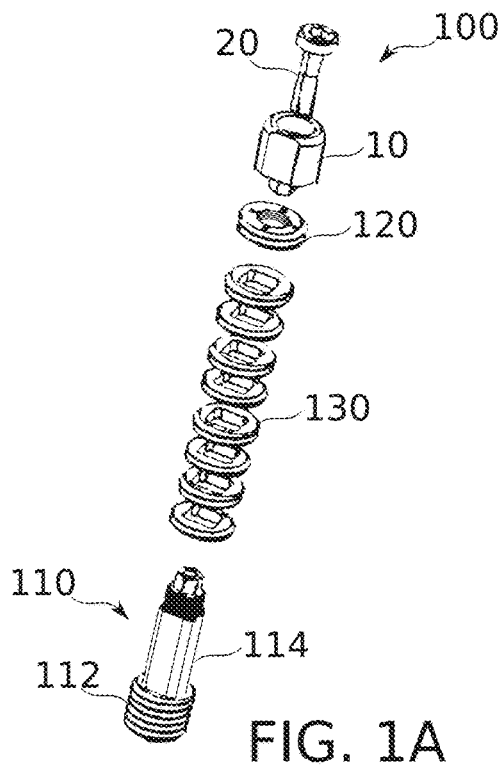
FIG. 1A schematically illustrates an exploded view of an implant assembly according to some exemplary embodiments of the present invention.
Figure 1B:
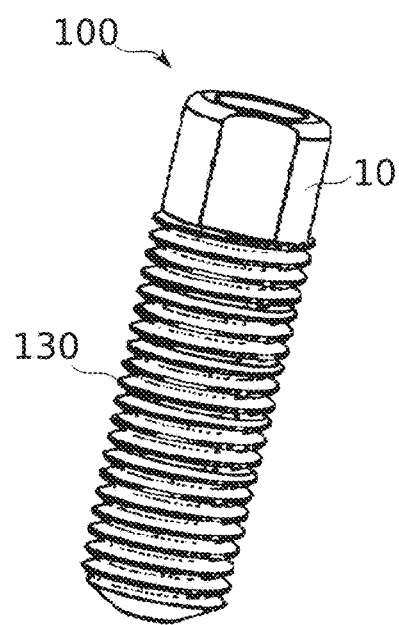
FIG. 1B schematically illustrates an assembled view of the exploded view depicted in FIG. 1A, according to some exemplary embodiments of the invention.

Reference is now made to FIG. 1A, which schematically illustrates an exploded view of implant assembly 100 according to some exemplary embodiments of the present invention. Reference is also now made to FIG. 1B, which schematically illustrates an assembled view of the exploded view depicted in FIG. 1A, according to some exemplary embodiments of the invention. Reference is also made to FIG. 1C, which schematically illustrates an assembled view of an optional implant anchor assembly 100 comprising acentric removable elements 135, according to some exemplary embodiments of the invention.

In some embodiments, implant assembly 100 comprises an implant for insertion into a jawbone, and more particularly, to a dental socket of a jawbone. In some embodiments, the implant assembly 100 acts as an anchoring base for other prosthetic devices, such as an abutment and/or crown.

In some embodiments, implant assembly 100 comprises an implant anchor core 110, and at least one or more removable elements 130, 135. Optionally, implant assembly 100 comprises at least one locking member 120. In some embodiments, implant anchor core 110 comprises an anchor (or distal portion) 112 and a core stem (or medial portion) 114 attached to the anchor 112. The anchor 112 comprises, for example, a distal base of the implant provided with means (such as screw threads) to securely engage bone surfaces in the distal region of a bone socket. In some embodiments, core stem 114 extends proximally from the anchor 112. Core stem 114 is recessed along its extent to create a volume to accommodate removable elements.

In some embodiments, anchor 112 and core stem 114 of implant assembly 100 provide an implant anchor allowing modular and/or reconfigurable assembly of removable elements 130, 135 to the implant. In some embodiments, an assembled implant assembly 100 includes concentric removable elements 130 disposed along a medial portion of an implant anchor core 110. Additionally or alternatively, acentric removable elements 135 are provided. Optionally, this provides an implant assembly with variable cross-section along its length.

Optionally, removable elements 130, 135 are removed and/or exchanged over time. Exchange is, for example, according to the state of the implant site, such as state of bone thickness, positioning, and/or the development of peri-implantitis. Accordingly, embodiments of the present invention provide a modular implant assembly capable of being fine-tuned and/or modified according to the evolution of the implantation site and in particular according to the development and/or developmental stages and/or evolution of peri-implantitis within the implantation site. In some embodiments, the implant assembly of the present invention provides an implant anchor capable of being accommodated to an implantation site as it evolves over time.

In some embodiments, implant assembly 100 provides a dental implant adapted for treatment peri-implantitis. Optionally, as peri-implantitis develops, a practitioner removes and optionally replaces removable elements 130 and/or locking member 120 along at least a portion of the infected area. Potentially, replacement of the removable elements allows for the infected area to heal properly. For example, a potentially infectious reservoir is removed along with the removable element. Optionally, a replaced removable element is the original removable element after cleaning, for example, after sterilization cleaning. Optionally, a removable element is replaced with another removable element of the same size and shape. Optionally, a removable element is replaced with another larger or smaller removable element.

In some embodiments, implant shapes are selected to have a particular surface relationship to the bone which surrounds them in the implant socket. For example, the shape is selected to exactly fit the bone socket walls, selected to be oversized to exert pressure on the bone socket walls, and/or selected to be undersized to create a gap between the implant surface and the bone socket walls. Combination of these options comprises, for example, variation as a function of depth within the socket, and/or variation as a function of radial position around the socket. Potentially, the relation of surfaces of implant assembly 100 and bone promotes and/or guides bone remodeling and/or osseointegration. Potentially, the relationship of surfaces protects the socket from infectious invasion. In some embodiments, the relationship of bone removable element surfaces to bone socket surfaces is changed over time. For example, as bone growth occurs, removable elements are replaced with smaller removable elements, creating a new space for bone growth to continue into. Additionally or alternatively, a removable element size is increased—for example, after loss of bone (due, for example, to infection, removal after infection, atrophy, or another reason).

In some embodiments of the invention, implant assembly 100 is coupled to any implant abutment 10 as is known in the art. Optionally, abutment 10 is secured to implant assembly 100 by means of an abutment screw 20 to couple the abutment to the implant anchor core 110.

Figure 2A:
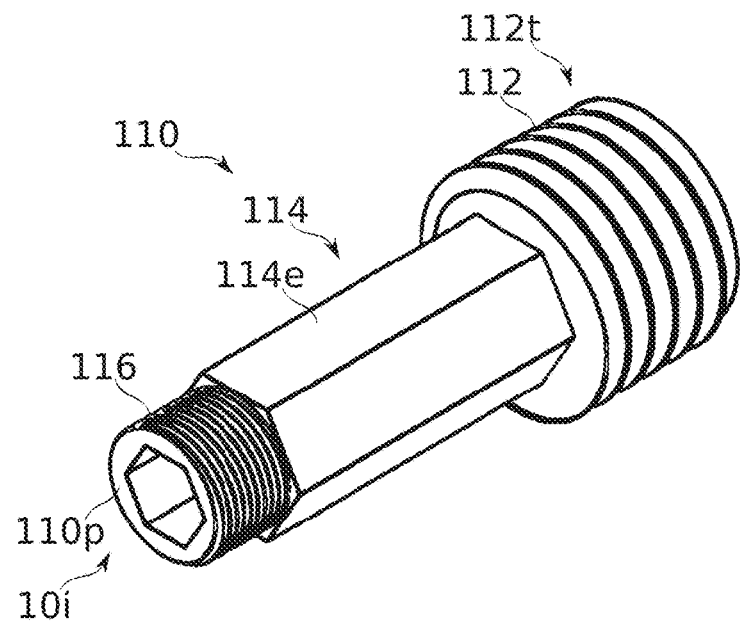
FIG. 2A schematically illustrates a perspective close up view of an optional anchor core according to some exemplary embodiments of the invention.
Figure 2B:
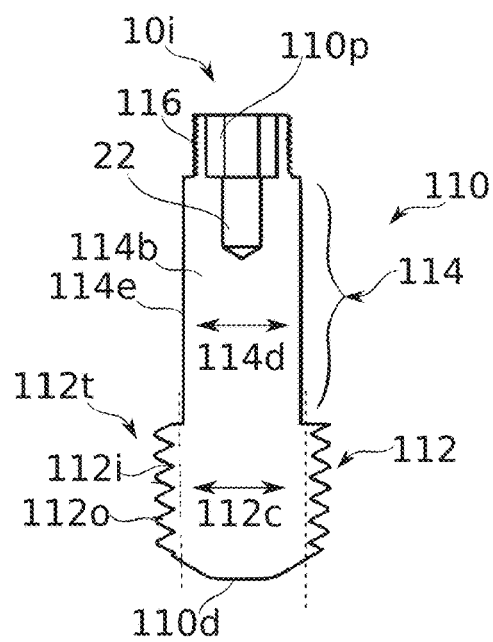
FIG. 2B schematically illustrates a cross sectional view of the implant anchor core depicted in FIG. 2A according to some exemplary embodiments of the invention.

Reference is now made to FIG. 2A, which schematically illustrates a perspective close up view of an optional anchor core 110 according to some exemplary embodiments of the invention. Reference is also made to FIG. 2B, which schematically illustrates a cross sectional view of the implant anchor core 110 depicted in FIG. 2A according to some exemplary embodiments of the invention.

In some embodiments, anchor core 110 comprises a proximal end 110p in the form of an internal connection platform 10i and abutment screw recess 22 used for coupling and associating with an abutment 10 and an abutment screw 20.

In some embodiments, implant anchor core 110 is provided in a substantially tubular body, the body comprising a distal end 110d and a proximal end 110p. Optionally, proximal end 110p is provided in the form of an abutment connection platform configured to receive an abutment 10. Optionally, abutment connection platform is configured as an internal, external and/or any combination thereof, or the like, tubular body of core 110. In some embodiments, core 110 comprises at least two portions including a distal portion 112 and a medial portion 114. In some embodiments, core 110 further comprises a proximal portion 116.

FIG. 2B reveals abutment screw recess 22. FIG. 2B further schematically illustrates the distal portion 112 in detail revealing the internal diameter 112i and outer diameter 112o. FIG. 2A shows medial portion 114 having an optional anti-rotational external surface along its length. The anti-rotational external surface is formed, for example, as hexagonal cross-section along the length of medial portion 114. In some embodiments, the anti-rotational surface comprises any non-circular cross-section, such as a convex or concave (e.g. star-shaped) polygon, ellipse or other oval, and/or crescent shape.

In some embodiments, distal portion 112 is defined adjacent to distal end 110d and extending proximally therefrom. Distal portion 112 comprises an anchoring portion of core 110 provided for anchoring implant assembly 100 within an implantation site. In some embodiments, distal portion 112 includes threading 112t provided for integrating with an implantation site. Optionally, threading 112t is configured according to any threading parameters as is known in the art for example including but not limited to pitch, number of starts, thread type, number of flutes, pitch angle, the like or any combination thereof.

In some embodiments of the invention, threading 112t defines an outer diameter 112o and an inner diameter 112i that are optionally configured according any threading parameters as is known in the art. In some embodiments, the outer diameter 112o defines the external surface of distal portion 112 while inner diameter 112i defines the internal diameter and distal portion core 112c of distal portion 112, for example as shown between dashed lines. Optionally, distal portion core 112c is configured to any profile shape as for example including but not limited to cylindrical, trapezoidal, tapered, screw-form, the like or any combination thereof.

In some embodiments of the invention, medial portion 114 is fluid with (integrally formed with) and extends from distal portion core 112c. Optionally, medial portion 114 extends proximally from the distal portion core 112c with a rod like body 114b configured to have an external surface 114e defining an external diameter 114d. In some embodiments of the invention, the external diameter of medial portion 114 is configured to have a smaller average diameter than the outer diameter 112o of distal portion 112. Optionally, external surface 114e is configured in optional non-rotational configuration, for example including polygonal having n sides where n is larger than 2, hexagon, pentagon, triangular, square, trapezoid the like or any combination thereof.

Optionally, medial portion 114 is configured to have threading along its length or a portion thereof.

In some embodiments, medial portion 114 is devoid of threading along its length. In some embodiments of the invention, medial portion 114 is configured and adapted to receive and/or associate with at least one removable elements 130, 135. In some embodiments, proximal portion 116 extends proximally from and is configured to be continuous with medial portion 114. In some embodiments of the invention, proximal portion 116 comprises threading 116t. Optionally, threading 116t is disposed along at least a portion of the length of proximal portion 116. Optionally threading 116t configured along the length of proximal portion 116. Optionally, proximal portion 116 is configured to received and/or associate with a removable element 130, 135; optionally a locking member 120. Optionally proximal end 110p is affixed to proximal portion 116 and is provided in the form of an optional abutment connection platform; for example, in the form of an internal platform or an external platform, the like, or any combination thereof.

Figure 3A:
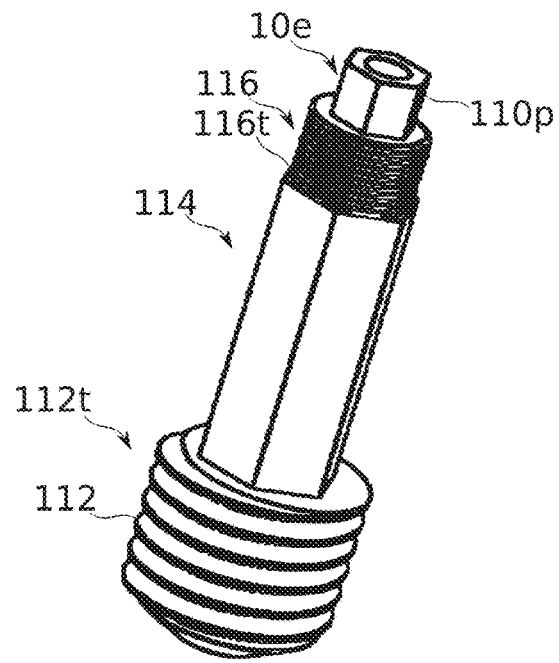
FIGS. 3A-3B schematically illustrate an optional embodiment of implant including a proximal end fittable to an external abutment connection platform, according to some exemplary embodiments of the invention.
Figure 3B:
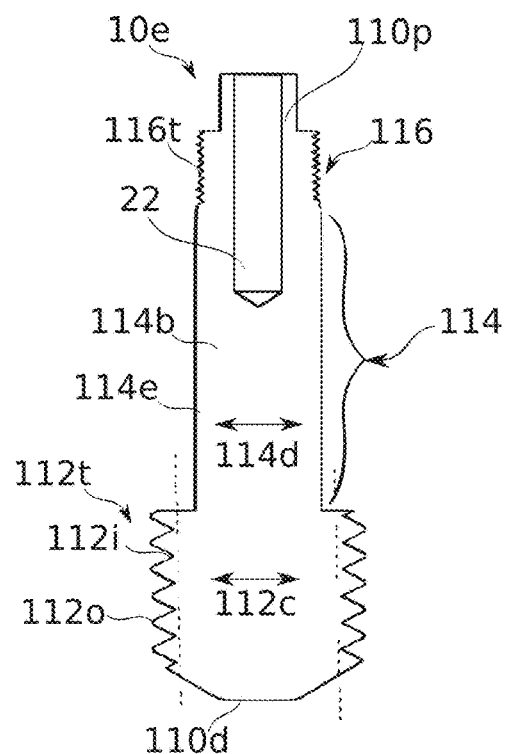

Reference is now made to FIGS. 3A-3B, which schematically illustrate an optional embodiment of implant 100 including proximal end 110p fittable to an external abutment connection platform 10e, according to some exemplary embodiments of the invention.

As shown in FIGS. 3A-3B, proximal end 110p is optionally provided in the form of an external hex 10e abutment connection platform that extends proximally from proximal portion 116. For example as shown in FIGS. 2A-2B proximal end 110p is optionally provided in the form of an internal hex 10i abutment connection platform. As shown internal hex 10i abutment connection platform is disposed internally with at least a portion of proximal portion 116 or with proximal portion 116 and at least a portion of medial portion 114.

Optionally, an abutment connection platform disposed along proximal end 110p is provided in optional forms as is known in the art for example including but not limited to an internal six receptor sockets, scalloped, internal dodecagon, external dodecagon, internal hex, external hex, external octagon, internal octagon, external spline, internal spline, morse taper, internal morse taper, one piece, internal six lobe, external six lobe, internal tri-lobe, external tri-lobe, internal six spline, external six-spline, internal thread, internal pentagon, external pentagon, external thread, internal square, external square, internal five lobe, internal four lobe, internal three spline, external triangle, internal eight spline, external six lobe, internal eight lobe, internal tube to tube plug in, triangular, polygonal of n sides where n>=3 or more, the like or any combination thereof.

Optionally, the external surface of anchor core 110 along any of its portions is provided with at least one or more form of an external surface treatment. Optionally, surface treatment is varied along different portions of core 110. For example, proximal portion 116 is provided with one form of external surface treatment while distal portion 112 is provided with a second form of external surface treatment, and medial portion 114 is provided with a third external surface treatment. Optionally, external surface treatment is selected from the group for example including but not limited to sandblast, SLA (Sand blast Large grit Acid etch), TPO (Titanium Porous Oxide), anodic oxidation, acid etching, CaP coating, TPS (Titanium Plasma Sprayed), HA (hydroxyapatite), machined/uncoated, RBM (Resorbable Blast Media), wet shot blasting (aluminium oxide), recrystallized hydroxyapatite, TCP (beta Tri-Calcium Phosphate coating), $TiO_2$ blast, fluoride hydrofluoric acid, blasted with hydroxyl apatite, SLA and NaCl solution, SBM (Soluble Blast Media), texture, glow discharge, titanium bead sintering, titanium-zirconium ceramic coating, titanium-niobium ceramic coating, $TiO_2$ coated, laser treatment, ASD (Anodic Spark Deposition), PRGF (Plasma Rich Growth Factors), titanium nitride coating, laser sintering, conditioning/hydroxylation, CaP coated, the like or any combination thereof.

In some embodiments of the invention, core 110 is provided as a single unitary member. Optionally, implant core 110 is provided from a plurality of portions that are coupled with one another to form the implant core structure 110. For example, distal portion 112 is an individual member that is coupled with an optional medial portion 114, for example via threading.

Figure 4G:
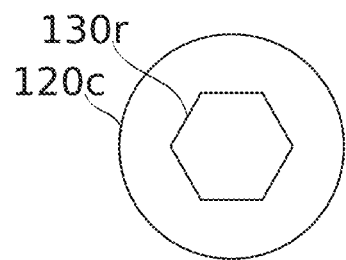
FIGS. 4G-4N show different relationships of concentric and acentric implant insert receiving bores to outer insert surfaces, according to some exemplary embodiments of the invention.
Figure 4H:
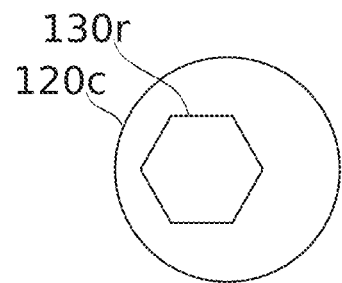
Figure 4I:
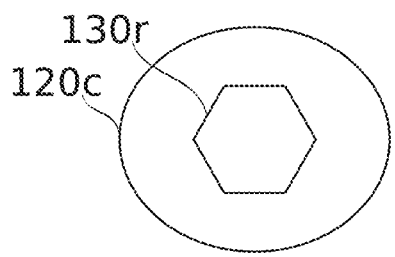
Figure 4J:
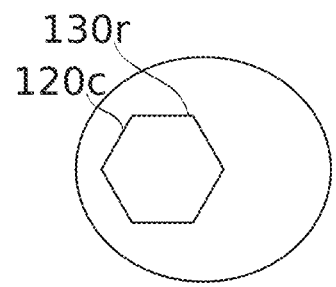
Figure 4K:
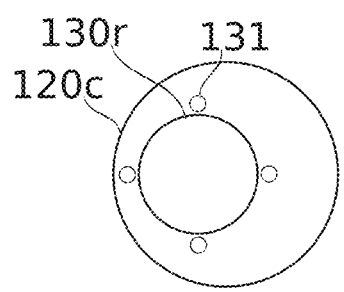
Figure 4L:
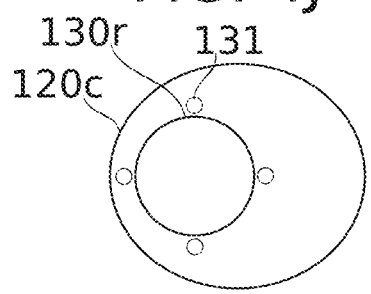
Figure 4M:
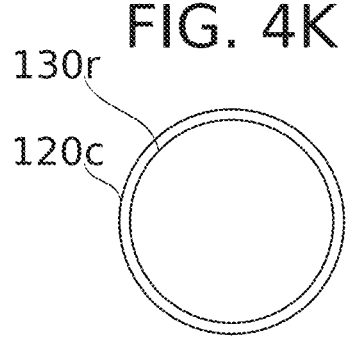
Figure 4N:
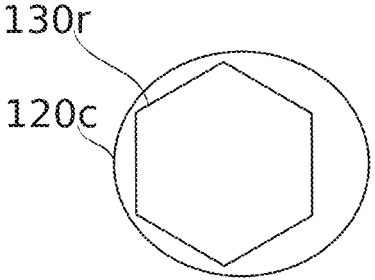

Reference is now made to FIG. 4A, which schematically illustrates a locking removable element 120 having a tooling interface 126 disposed along upper surface 120a, according to some exemplary embodiments of the invention. Reference is also now made to FIGS. 4B-4D, which schematically illustrate exemplary removable elements 130, according to some exemplary embodiments of the invention. Reference is also made to FIGS. 4E-4F, which schematically illustrate perspective views of acentric removable element 135, according to some exemplary embodiments of the invention.

Removable elements 130, 135, 120, detailed in FIGS. 4A-4F, are provided to be associated over at least a portion of anchor core 110; for example, along the length of medial portion 114 and proximal portion 116.

In some embodiments, removable elements are provided in a ring form. In some embodiments, a removable element is longer in form than the short rings shown in FIGS. 4A-4F; for example, the removable element extends the full length of medial portion 114, or any shorter length of medial portion 114. In some embodiments, removable elements are partial rings. For example, the partial ring adjoins the medial portion 114 around 90% of the circumference of medial portion 114, around 75%, around 50%, around 33%, around 25%, or around another greater, lesser, or intermediate amount of the circumference of the medial portion.

In some embodiments of the invention, removable elements 130, 135, 120 have an upper surface (130a, 120a), a lower surface (130b, 120b) that are coupled with an external circumferential surface (130c, 120c) and having a receiving bore (130r, 122, 132, 135a) defined between upper surface (130a, 120a) and lower surface (130b, 120b).

In some embodiments of the invention, external circumferential surface (130c, 120c) is a textured surface provided for inducing and/or promoting osseointegration. Optionally, surface 130c is provided in the form of threading. Optionally threading disposed along surface 130c is configured to be continuous with threading 112t disposed along distal portion 112.

Optionally, external circumferential surface (130c, 120c) is coated with a medicament and/or agent and/or therapeutic agent and/or controlled release agent provided to promote osseointegration and/or treatment of peri-implantitis and/or prevention of peri-implantitis.

Optionally any portion and/or surface of removable elements 130, 135, 120 is coated with a medicament and/or agent and/or therapeutic agent and/or controlled release agent provided to promote osseointegration and/or to treat peri-implantitis and/or to prevent of peri-implantitis. Optionally, the surfaces or portion of a surface that is coated includes but is not limited to upper surface (130a, 120a), and/or lower surface (130b, 120b), bore (122, 130r, 135a, 132), the like or any combination thereof.

Optionally, any portion and/or surface of removable elements 130, 135, 120 along any of their portions is provided with at least one or more form of an external surface treatment. Optionally, surface treatment is varied along different removable elements 130, 135, 120 and different portions of each of removable elements 130, 135, 120. For example, external circumferential surface 130c, 120c is provided with one form of external surface treatment while upper surface 130a, 120a is provided with a second form of external surface treatment, and lower surface 130b, 120b is provided with a third external surface treatment. Optionally, external surface treatment is selected from the group for example including but not limited to sandblast, SLA (Sand blast Large grit Acid etch), TPO (Titanium Porous Oxide), anodic oxidation, acid etching, CaP coating, TPS (Titanium Plasma Sprayed), HA (hydroxyapatite), machined/uncoated, RBM (Resorbable Blast Media), wet shot blasting (aluminium oxide), recrystallized hydroxyapatite, TCP (beta Tri-Calcium Phosphate coating), $TiO_2$ blast, fluoride hydrofluoric acid, blasted with hydroxyl apatite, SLA and NaCl solution, SBM (Soluble Blast Media), texture, glow discharge, titanium bead sintering, titanium-zirconium ceramic coating, titanium-niobium ceramic coating, $TiO_2$ coated, laser treatment, ASD (Anodic Spark Deposition), PRGF (Plasma Rich Growth Factors), titanium nitride coating, laser sintering, conditioning/hydroxylation, CaP coated, the like or any combination thereof. Optionally, the surfaces or portion of a surface that is coated may for example include but is not limited to upper surface (130a, 120a), and/or lower surface (130b, 120b), bore (122, 130r, 135a, 132), the like or any combination thereof.

Optionally, receiving bore 130r is configured to be a central bore 132 that is disposed centrally between the upper surface 130a and lower surface 130b. Optionally, receiving bore 130r is configured to be an acentric bore 135a that is disposed a-centrically and/or off centered between the upper surface 130a and lower surface 130b, therein defining an acentric removable element 135, for example as shown in FIGS. 1C, and 4E-4F. In some embodiments, concentric and acentric implants 130, 135 are used for example, in a mixed concentric/acentric configuration.

In some embodiments of the invention, central bore 132 comprises an anti-rotational surface configuration for example as shown in FIGS. 4B-4D. For example, removable element 135 comprises an anti-rotational receiving bore 135a having a hexagonal configuration to match that of an implant anchor medial portion 114. Also for example FIG. 4B shows removable element 130 having a central bore 132 having an anti-rotational surface in a polygonal (square) configuration. FIGS. 4C-4D show an optional concentric removable element 130 having a hexagonal anti-rotational receiving bore configuration 132.

Optionally, receiving bore 130r is configured to have threading 124 disposed along its inner surface, for example defining a threaded receiving bore 122, for example as shown in FIG. 4A. Optionally, anchor core 110 provides for receiving at least one or more optional removable elements 120, 130, 135. In some embodiments of the invention, removable elements 130, 135 are stacked along the length of medial portion 114, and locked into position and/or pressed one on top of the other with an implant locking member 120 that is disposed over proximal portion 116.

Optionally, removable element 130, 135, 120 is configured to have a transitional profile configuration wherein the removable element may interchangeably assume a small profile configuration having a small diameter and/or an expanded profile configuration having a large diameter. Optionally, the transitional profile configuration is provided about at least one or more surfaces of removable element for example including but not limited to upper surface, lower surface, circumferential surface, bore or the like.

Optionally, implant locking member 120 comprises a tooling interface 126 disposed along at least one of the upper surface 120a, and/or lower surface 120b, and/or circumferential surface 120c, a threaded receiving bore 122, any combination thereof or the like. Optionally, tooling interface 126 provides for facilitating maneuvering locking member 120 along the length of proximal portion 116. Optionally, tooling interface 126 is provided for interfacing with a dedicated tool provided for manipulating and/or controlling locking member 120.

In some embodiments of the invention, receiving bore 130r is configured to assume various forms for example in the form of bores 122, 135a, 132, that are configured to have at least one of threading, for example bore 122, or an anti-rotational surface, for example 135a, 132, that match and/or correspond to the external surface of proximal portion 116 and/or medial portion 114 respectively.

Reference is now made to FIGS. 4G-4N, which show different relationships of concentric and acentric removable element receiving bores 130r to outer removable element surfaces 120c, according to some exemplary embodiments of the invention.

As described also in relation to FIGS. 4A-4F, in some embodiments, receiving bore 130r and removable element surface 120c are concentric (for example, FIGS. 4G, 4I, and 4M); in some embodiments, the relationship is acentric (for example, FIGS. 4H, 4J, 4K, 4L, and 4N). In some embodiments, the outer removable element surface 120c is substantially circular (FIGS. 4G, 4H, 4K, and 4M).

In some embodiments, another outer surface shape is provided. For example, an elliptical shape is shown in FIGS. 4I, 4J, 4L, and 4N. It is to be understood that any other non-circular shape is optionally provided. In particular, shapes which are generally ovoid, and/or comprise a substantially circular profile provided with one or more bulging regions are optionally provided. In some embodiments, an implant is provided which is manufactured (for example, 3-D printed) according to the particular measurements of an individual insertion site. However, it is a potential advantage to provide pre-manufactured removable elements which are suitable for a range of actual implant site morphologies, for example, for reasons of regulatory and/or quality control, choice of material and/or manufacturing processes, and/or reduction of time/effort required at the time of implantation.

In some embodiments, removable elements are provided which cover a range of potential dental configurations by means of parts which are selectable from among a predetermined range of choices, and/or adjustable in position with respect to one another and/or the mouth anatomy. In some embodiments, the shape-locking interaction of the receiving bore 130r with the core shaft (medial portion) 114 allows positioning each implant in one of n rotationally differentiated positions, where n is a number of distinct shape locked positions (for example, 2, 3, 4, 6 or another number of positions). Illustrated is a 6-way locking shape, but it is to be understood that other shapes are optionally provided (for example, square, oval, pentagonal, and/or star-shaped or otherwise concave). In some embodiments, flexibility for positioning is further provided by the rotational position of the implant within the receiving bone socket (for example, there are optionally 60 degrees of positioning freedom for each face of a regular hexagonal shaft relative to bone). In some embodiments, there is just one shape-locked position, and selection of removable element orientation is fully by the rotational position of the shaft. In some embodiments, there is no rotational shape locking (for example, medial portion 114 is circular). Optionally, such a removable element is positioned and/or finds its position as it is pressed into the socket. Rotational motion afterwards is limited, for example, by the fit of the implant inset to the implant core (friction fit), by the locking constraints of the bone socket itself, and/or by a further locking step, such as a locking pressure applied longitudinally along the implant length via a locking member such as locking member 120. Optionally, rotational locking is created or assisted by spatial interactions among removable elements along the longitudinal direction—for example, removable elements are provided with one or more inset and/or protruding regions 131 (FIGS. 4K, 4L) on a face transverse to the longitudinal axis of the removable element.

In some embodiments, a range of acentric offsets for a removable element is provided, for example, as part of an implant kit. For example, an implant provides a choice of no acentric offset, an acentric offset of about 1 mm, an offset of about 1.5 mm, and/or an offset of about 2 mm. As described also in relation to FIGS. 6A-6C: in some embodiments, removable elements comprise a plurality of layers. In some embodiments, one or more of the layers provides an eccentric protrusion which can be alternatively stripped to better match the morphology of the implant site, or left on for initial implantation (this option is in addition to options for modifying removable elements after implantation as described in relation to FIGS. 6A-6C).

In some embodiments, removable element wall thickness is, for example, about 50-150 μm, 100-300 μm, 200-400 μm, 300-500 μm, 400-800 μm, 500-1000 μm, 800-1600 μm, or another range having the same, larger, smaller, and/or intermediate bounds. In some embodiments, the ratio of removable element wall thickness to the thickness of core shaft 114 is relatively large in at least one portion of the removable element wall—for example, about 1:2, 1:3, 1:4, or another greater, lesser, or intermediate thickness. Potentially, this provides a potential advantage for cases where the bore of the implant site is relatively open (wide) at a proximal position. Potentially, this allows easier handling of longitudinally short removable elements (ring-like, for example); providing strength to resist breakage under forces of insertion and/or removal. Such relatively thick walls are shown, for example, in FIGS. 4G-4L and 4N. In some embodiments, the ratio is relatively small: for example, about 1:10, 1:15, 1:20, or another larger, smaller, or intermediate ratio. A thin-walled removable element provides a potential advantage for maintaining an approximately functionally equivalent implant shape even upon removal of the removable element. For example, a 4 mm wide removable element includes a removable element having a 150 μm thick wall. If the removable element is removed (for example, due to later development of peri-implantitis), the remaining implant still retains over 90% of its original width. Potentially, this width is still enough for supporting implant functions such as osseointegration, and/or the strength of the implant body itself. Thin walled removable elements and their use are also discussed in relation to FIGS. 6A-6C, hereinbelow.

Figure 5:
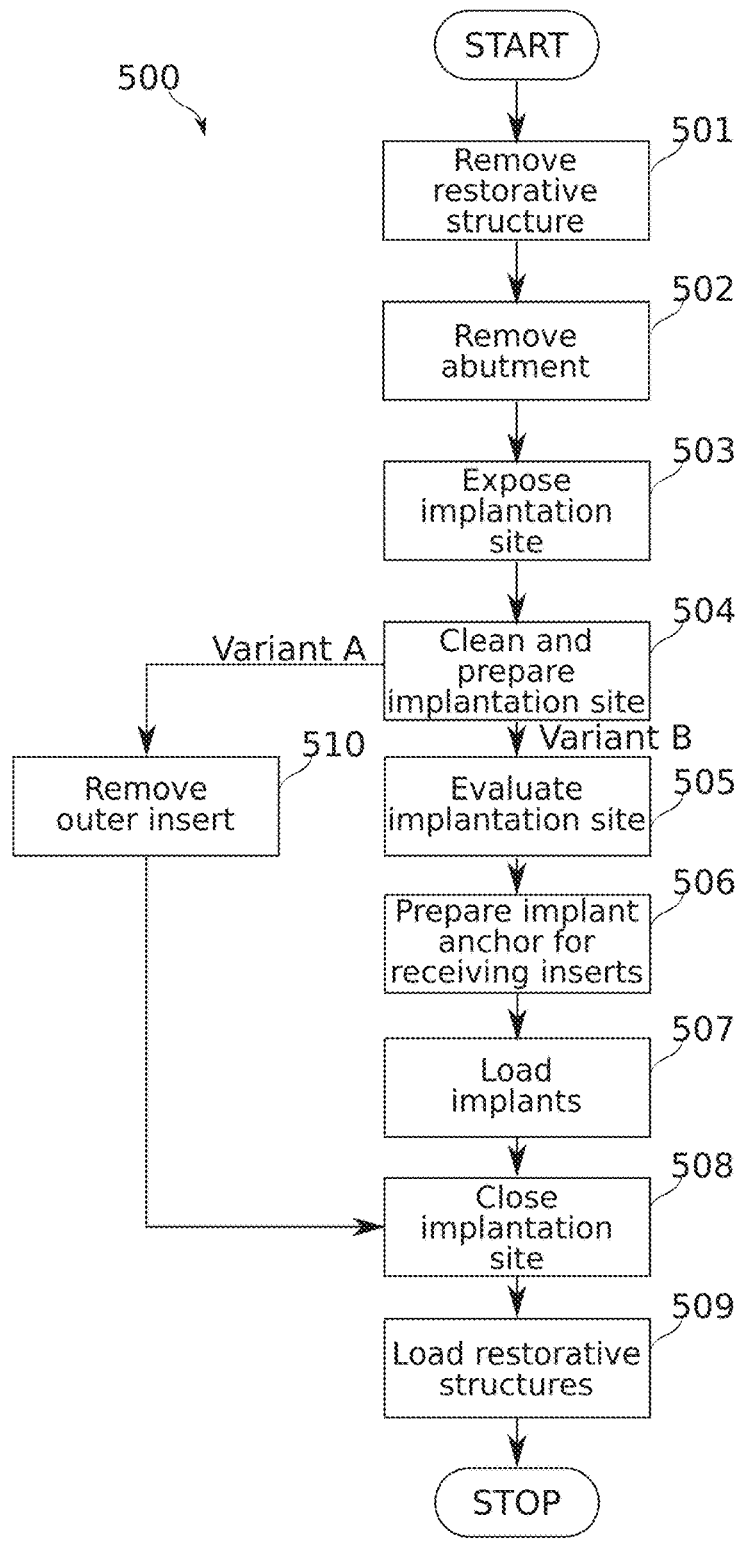
FIG. 5 is a flowchart of a method for treating peri-implant disease, according to some exemplary embodiments of the invention.

Reference is now made to FIG. 5, which is a flowchart of a method 500 for treating peri-implant disease, according to some exemplary embodiments of the invention.

Method 500 describes steps taken to treat peri-implantitis identified in an implantation site.

At block 501, in some embodiments, a practitioner removes the restorative structure and/or prosthetic members of an implant assembly, for example a crown, bridge, or the like.

At block 502, in some embodiments, the implant abutment 10 is removed.

At block 503, in some embodiments, the implantation site is exposed to reveal the infected area within the anchor implantation site.

At block 504, in some embodiments, the exposed implantation site is cleaned to remove any infected tissue.

Variant A of the method is performed with implants having removable sleeves (or removable rings, sleeve portions, ring portions, strips, wrapping, or other removable element type), the removal of which exposes a surface underneath which is suited to become the new outer surface of the bone implant. In some embodiments, this suitability comprises a surface treated for osseointegration. Variant A continues from block 504 to block 510, in some embodiments, with removal of an outer removable element (for example, removal of a sleeve removable element).

Variant B of the method is performed with implants having removable/replaceable implants, and continues from block 504 to block 505, in some embodiments, an evaluation of the height of bone loss and implant anchor holding force is undertaken by a practitioner.

At block 506, in some embodiments, the implant anchor is prepared for receiving at least one or more removable elements. Optionally, the removable elements disposed on implant anchor core 110 are removed from the implantation site. Optionally, if an "over the counter" (OTC) implant is to be used, it is prepared for retrofitting and/or receiving at least one or more removable elements 130, 120, 135 according to the present invention. Optionally, preparing an OTC implant is performed with optional proprietary and/or customized tools.

In some embodiments of the invention, the proprietary and/or customized tools are used to reduce the external surface of the OTC implant in preparation for receiving at least one or more optional removable elements according to the present invention.

At block 507, in some embodiments, the implant anchor is loaded with at least one or more removable element to cover at least a portion of the length of the infected area by peri-implantitis and/or bone loss region identified in stage 504.

At block 508, in some embodiments, the clean implantation site is closed.

At block 509, in some embodiments, the restorative structures—for example including the abutment, crown and/or bridge—are reintroduced over implant assembly 100, and flow chart 500 terminates.

Figure 6A:
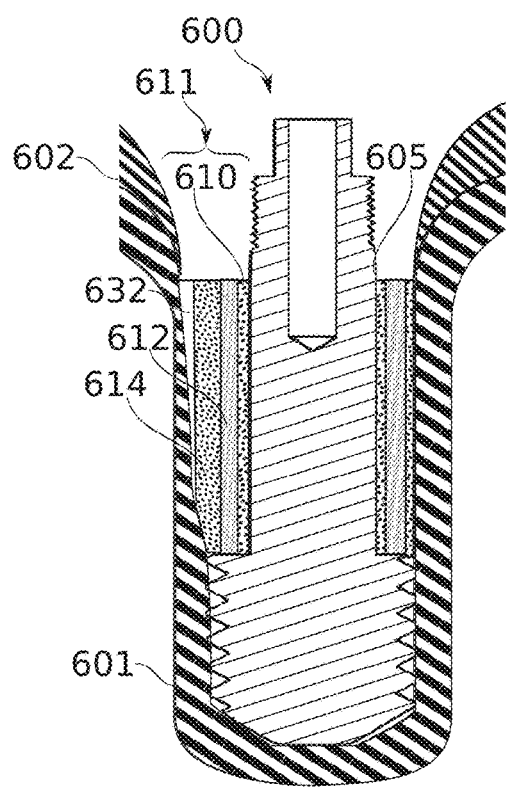
FIGS. 6A-6C illustrate a multi-layered implant insert for use with a dental implant having an anchor core, according to some exemplary embodiments of the invention.
Figure 6B:
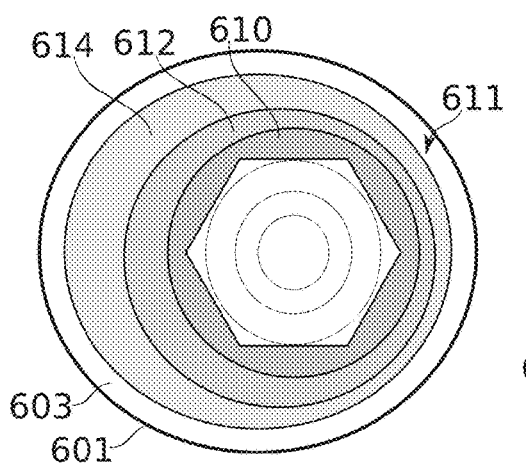
Figure 6C:
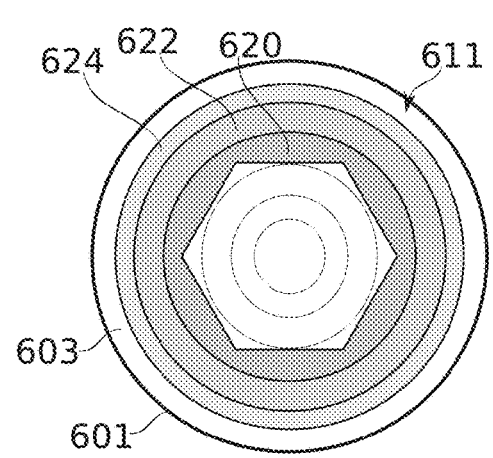

Reference is now made to FIGS. 6A-6C, which illustrate a multi-layered removable element 611 for use with a dental implant 600 having an anchor core 605, according to some exemplary embodiments of the invention.

In some embodiments, a removable element 611 is provided in the form of a plurality of layers 610, 612, 614, 620, 622, 624 (FIG. 6A shows layers from a cutaway side view; FIGS. 6B and 6C show exemplary layer arrangements from a top view). Optionally, the removable element 611 is in the form of a sleeve or ring. Optionally, the removable element 611 comprises one or more strips, with the layers provided as individual strips overlapping, and/or as layers of a single strip. Optionally, a strip removable element is wrapped around the anchor core 605, and layers of the strip comprise different windings of the strip removable element. Optionally, a plurality of strip, sleeve portion and/or ring portion removable elements are provided. Optionally, one, two, or more removable elements 611 are provided—a single removable element extending along the implant body, or a plurality of removable elements: for example, stacked removable elements along the implant body, and/or a plurality of removable elements covering different longitudinal extents along the implant body.

In some embodiments, layers 610, 612, 614, 620, 622, 624 are separately removable from the implant. In some embodiments, each layer comprises an outer surface treated for osseointegration, for example by coating and/or roughening treatment during manufacture of the implant and/or removable element. An embodiment having nested layers of removable element bearing osseointegrating surfaces is detailed in relation to FIGS. 8A-8C, hereinbelow. Such an implant has potential advantages for the management of peri-implantitis, also as described in relation to FIGS. 8A-8C.

However, other layer arrangements and compositions are also provided in some embodiments of the invention. Optionally, the layers are provided with different properties, and optionally removed according to the current requirements for treatment. For example, in some embodiments, a first (optionally, outer) layer is provided which comprises functions specialized for treatment of a peri-implantitis condition, and/or support during healing. For example, the layer is impregnated with medicaments having antibacterial properties. Optionally, the outer layer comprises a bioresorbable material such as: a bioresorbable polymer, for example, a polyhydroxy acid; bioresorbable metal; and/or bioresorbable ceramic. Optionally, the removable element layer is mechanically removable, for example by pulled extraction, and/or by use of a center pin trephine aligned to remove a selected section of the implant by cutting into it. Optionally, a removable element layer is attached to a portion of the implant capping apparatus, for example, a capping segment (such as locking member 120) and/or an abutment. An integrated abutment-sleeve embodiment is described, for example, in relation to FIGS. 7A-7C.

In some embodiments, a second (optionally, inner) layer is provided for a second post-implantation phase, for example, osseointegration. In some embodiments, multiple osseointegration layers are provided (optionally separated by a spacing layer). Optionally, a failed or infected osseointegration layer is removed (drilled or pulled, for example), leaving behind a new surface. Compared to simply drilling out concentric rings of the implant, it is a potential advantage to supply physically separate sleeves to provide a correctly textured surface upon removal of the outer layer, rather than whatever texture the drilling operation creates (a drilled out surface as such is generally not suitable for osseointegration). Potentially, use of spacer sleeves also allows greater certainty of the degree of layer removal. For example, a spacer layer between two osseointegrating surfaces decreases a requirement for tight tolerances in the use of a center pin trephine. Optionally, the osseointegrating surface removable element layer is relatively thin compared to the spacer layer, making it relatively easy to target. Optionally, a spacer layer between a first and second osseointegrating layer is bioresorbable to fully expose a second osseointegration surface even if imperfectly removed during initial exposure. Optionally, layered manufacture using alternate materials allows use of coating technologies which nevertheless keep each coating layer intended for osseointegration exposure separate from the layer beneath.

In some embodiments, layers are shaped (by their thickness and/or extent) so that they are adapted and/or adaptable to the shape of a bone socket. For example, the left-side portion of bone 601 in FIG. 6A (underneath gingival layer 602) comprises an asymmetrically wider region 632. In some embodiments, removable element layers 610, 612, and/or 614 are also expanded (thicker) in some portion (compared to another portion; e.g., of different thicknesses around a radial dimension, and/or along a longitudinal direction) allowing the space to be more completely filled. A sufficiently small remaining gap is potentially filled by later bone regrowth, if other appropriate conditions for bone regrowth are met. FIG. 6B illustrates a top view of such an implant, where bony wall 601 is separated from removable element 611 by a gap 603, the gap being maintained (in this case) at an approximately even distance around the implant. In some embodiments, the amount of eccentricity (acentricity) provided by each of a sequence of removable element layers 614, 612, 610 changes between layers. For example, an outer layer 614 is optionally a bioresorbable layer, which supports and/or promotes bone growth, but is itself destroyed in the process. Potentially, this allows an initially thin bone region space in which to regrow for strengthening itself, before it encounters the hopefully permanent implant wall. Nevertheless, there are, in some embodiments, one or more additional removable element layers, which potentially constitute a removable reserve in case of peri-implantitis requiring further treatment and implant surface renewal.

Reference is now made to FIGS. 7A-7C, which schematically illustrate an implant 700 provided with an abutment 725 having a sleeve region 727 which extends along a medial portion (core shaft) 714 of the core implant body, according to some exemplary embodiments of the invention. Reference is also made to FIGS. 7D-7G, which schematically illustrate the abutment/sleeve assembly 726, according to some exemplary embodiments of the invention.

In some embodiments, dental implant 700 comprises the three major parts shown in exploded view in FIG. 7C—integrated abutment/sleeve 726 (comprising abutment 725 and sleeve 727), implant body 713 comprising distal anchor 712 and shaft 714, and abutment screw 720 which inserts to connect the two other pieces together.

In some embodiments, the sleeve-abutment assembly provides advantages of a replaceable/renewable implant surface by extending sleeve 726 (which is optionally treated for osseointegration) into an intrabony region of the bone socket to which the implant is anchored. Optionally, the surface of region 714 is also treated for osseointegration (for example, roughened, treated with hydroxyapatite, or otherwise treated for bone integration as known in the art).

Optionally, sleeve-abutment 726 is removed upon discovery of peri-implantitis. Optionally, it is replaced with a normal abutment, and the surface of shaft 714 becomes the new exposed intrabony surface of the implant. Alternatively, the sleeve-abutment is replaced by a new sleeve-abutment. It should be noted that normally, osseointegration of the abutment sleeve tends to fix the abutment into place. Thus, the abutment is optionally considered permanent once installed, barring later complications which require surface renewal.

An integrated (or monoblock, or integrally formed) abutment-sleeve provides potential advantages over an abutment-sleeve assembly, by removing the potential weak and/or vulnerable (to infection, and/or to mechanical damage) region of their joining. Furthermore, the sleeve potentially supports the abutment at its widest perimeter, reducing vulnerability to failure in a torquing mode.

Figure 8D:
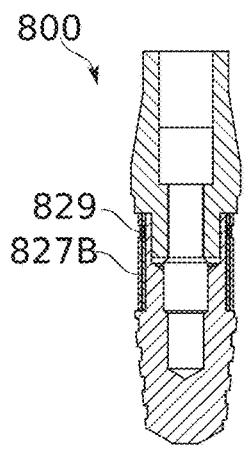
FIGS. 8D-8I schematically illustrate the implant in sequential stages of layer removal, according to some exemplary embodiments of the invention.
Figure 8E:
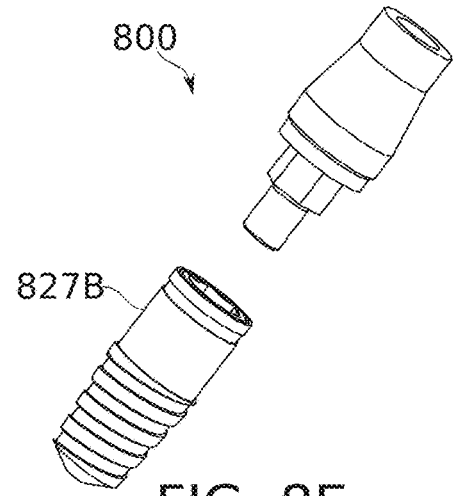
Figure 8F:
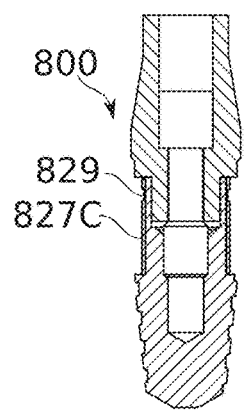
Figure 8G:
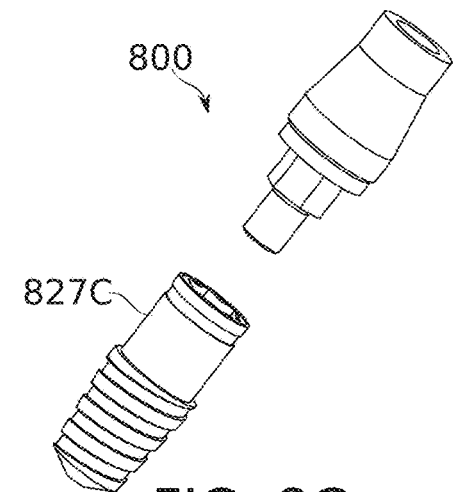
Figure 8H:
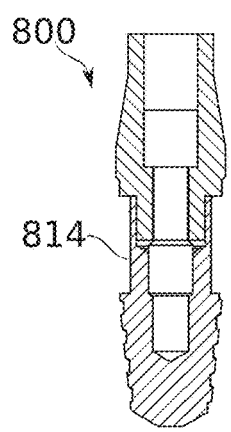
Figure 8I:
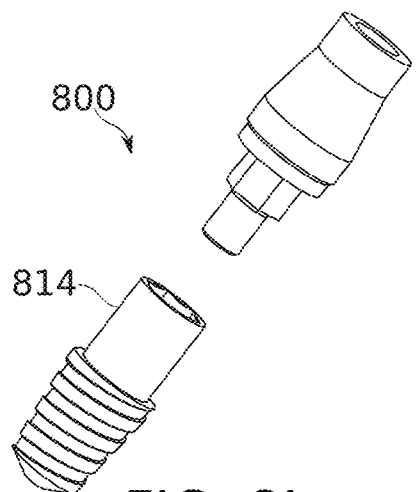

Reference is now made to FIGS. 8A-8C, which schematically illustrate an implant 800 comprising a removable element region 827 comprising a plurality of separately removable layers 827A-827C, according to some exemplary embodiments of the invention. Reference is also made to FIGS. 8D-8I, which schematically illustrate the implant 800 in sequential stages of layer removal, according to some exemplary embodiments of the invention.

In some embodiments, each of layers 827A, 827B, 827C (optionally more or fewer layers are provided), and optionally the surface of implant shaft 814, are treated to promote osseointegration. Each sleeve is separately removable, for example, upon discovery of contamination that requires refreshing the implant surface. This potentially provides an implant with new or refreshed surfacing through a plurality of peri-implantitis events (four, for example; with FIGS. 8A-8C representing a new implantation configures, and FIGS. 8D-8E, 8F-8G, and 8H-8I representing the implant state with newly exposed surfaces 827B, 827C, and 814 after removal of the first, second, and third removable elements, respectively).

In some embodiments, extraction of a sleeve is facilitated by inset region 829, which provides a surface that can be gripped from the proximal side of the implant and pulled off. Additionally or alternatively, extraction is by center-pin trephine drill, and/or by cutting one or more slits along the body of the sleeve to open it. Extraction is after removal of abutment screw 820 and abutment 825 (abutment 825 fits to the implant body, for example, at receiving socket 828 by a matching mating element 826). In some embodiments, the sleeve-protected region of the implant extends up to a distal anchor region 812, which is sufficiently deep in the bone that it is reasonably unlikely to become infected itself.

In some embodiments, the overall implant is, for example, in the range of about 10-25 mm long. In some embodiments, the wall thickness of each sleeve layer is within the range, for example, of about 50-100 μm, 75-150 μm, 100-200 μm, 125-300 μm, 250-400 μm, any range defined by the overlap of two or more of those ranges, any range defined by including values of just one of those ranges, and/or another range having the same, larger, smaller, and/or intermediate bounds.

Reference is now made to FIGS. 12A-12F, which schematically illustrate assembled and disassembled perspective, sectional, and facing views of an implant 1200 having a single removable element 1227, according to some exemplary embodiments of the invention.

In some embodiments, implant 1200 comprises a single removable element 1227, which is optionally formed as a sleeve extending along a shaft region 1214. In some embodiments, an inset region 1229 is provided on removable element 1227 to facilitate removal.

Otherwise, the implant 1200 comprises major portions of the implant assembly described in previous embodiments; for example, anchoring base 1212, shaft 1214, abutment 1225, and abutment screw 1220.

Figure 9A:
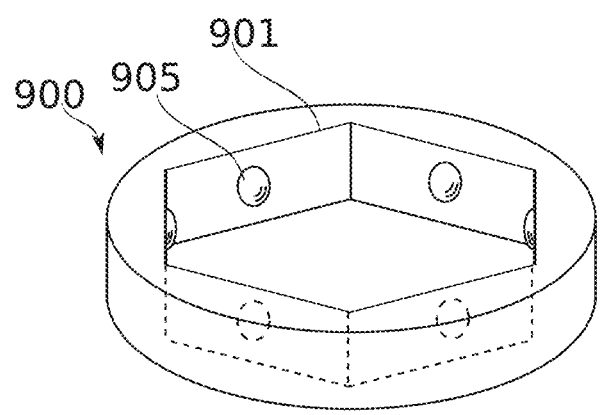
FIGS. 9A-9B schematically illustrate protrusions on an implant insert, according to some exemplary embodiments of the invention.
Figure 9B:
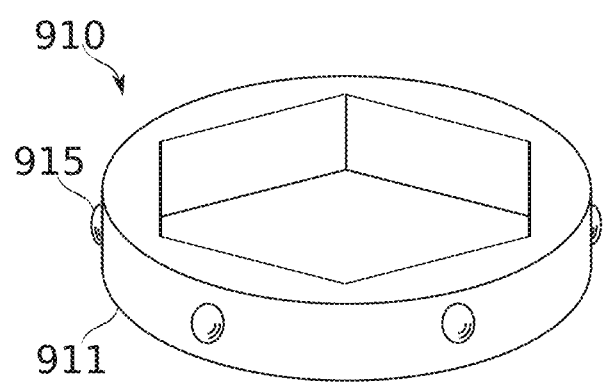

Reference is now made to FIGS. 9A-9B, which schematically illustrate protrusions on a removable element 900, 910, according to some exemplary embodiments of the invention.

Inserts 900, 910 optionally represent whole removable elements (for example, rings), slab sections of removable elements (for example, parts of a sleeve), and/or single sleeves or rings of a multi-sleeve or multi-ring removable element.

In some embodiments, a removable element 900, 910 is manufactured with surface elevations 905, 915 which interact with an adjoining surface by contact. For example, surface elevations 905 line the lumenal surface 901 of implant 900; surface elevations 915 line the outer surface 911 of implant 910. In some embodiments, a complementary indentation, channel, or other shape is provided on a mating part (another removable element part, or a part of the implant core). Potentially, this interference augments or replaces a friction/surface roughness fit. Optionally, the channel is transverse to the longitudinal direction, and provides a locking stop which holds the removable element in place longitudinally. In some embodiments, a mating part is provided with longitudinal channel, along which the elevations 905, 915 travel when the removable element is inserted onto the implant. Optionally, rotating the removable element tends to push the surface outward, resulting in a slight expansion. Potentially, the expansion helps to fit the sleeve to its bony surroundings.

Reference is now made to FIGS. 10A-10D, which schematically illustrate an implant having an eccentrically placed core shaft 114, for use with a removable element which optionally has an acentric receiving bore 130r, according to some exemplary embodiments of the invention.

Figure 10A:
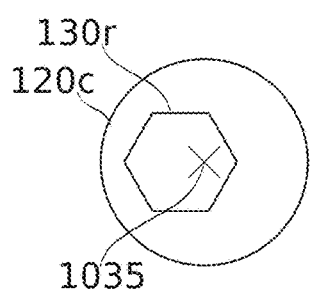
FIGS. 10A-10D schematically illustrate an implant having an eccentrically placed core shaft, for use with an implant insert which optionally has an acentric receiving bore, according to some exemplary embodiments of the invention.
Figure 10B:
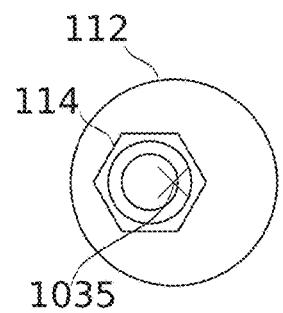
Figure 10C:
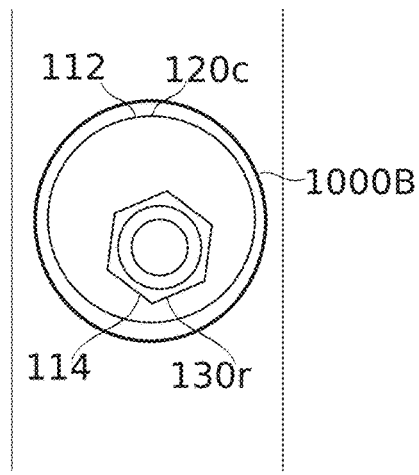
Figure 10D:
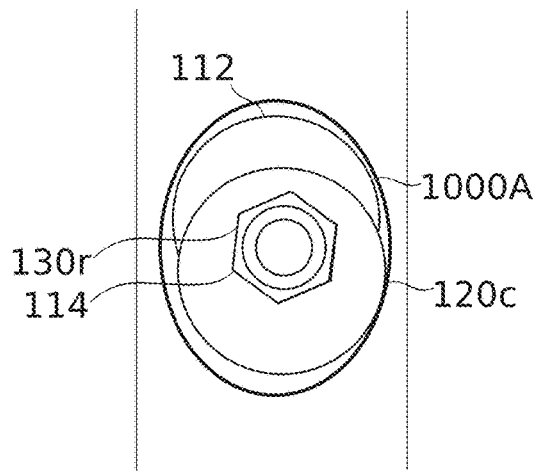

FIG. 10A schematically represents a top view of a removable element embodiment having an outer circumference 120c, and an inner receiving bore 130r. The inner receiving bore is offset from removable element radial center 1035. FIG. 10B schematically represent as top view of an implant core embodiment comprising anchor base 112 and shaft 114, with shaft 114 also offset from the radial center 1035.

Optionally, the two eccentric locations are used together in one or more of the following fashions.

In some embodiments, implant core 114 is loaded with acentric removable elements such that outer surface 120c and the radial extent of base 112 are aligned (optionally, they coincide, and/or are concentric). This configuration is suitable, for example, during screw implantation, as it provides a circularly symmetric configuration allowing rotation through the bone socket.

Optionally, this is also the final configuration, used, for example, with an implantation site such as socket 1000B where the bone socket is generally circular.

However, in some instances, there is an implantation site 1000A which includes a region of bone atrophy, offset from the core, which it is desirable to fill. Optionally, the core shaft 114 itself is rotated to a position, for example, a position which is more central to the socket of the implantation site. Then, a position of the removable element on the core shaft is chosen which, instead of creating a concentric configuration, creates an off-center configuration which substantially fills the shaft. In this way, by choosing different combinations of implant rotational positions and removable element rotational positions, a large range of different space-filling implant configurations are optionally provided. In some embodiments, more than one orientation is used; for example, "centric" and "acentric" positions are alternately filled by disk- or ring-like removable elements along the implant. Potentially, this creates an implant shape with greater extent for supporting osseointegration (and/or bone ingrowth) than would be possible for an implant with a strictly circular cross-sectional profile.

Figure 11A:
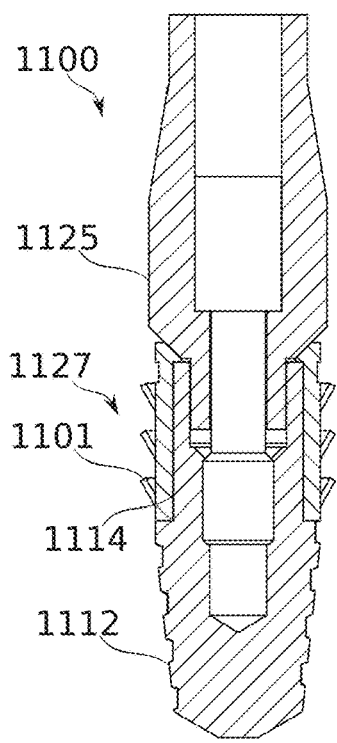
FIGS. 11A-11C schematically illustrate an implant provided with an insert sleeve comprising outward pressing elements, according to some exemplary embodiments of the invention.
Figure 11B:
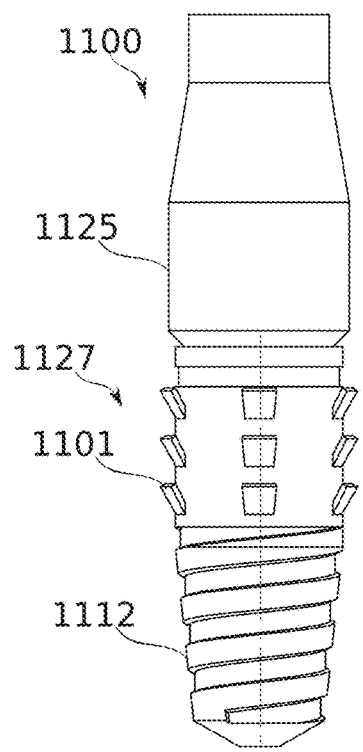
Figure 11C:
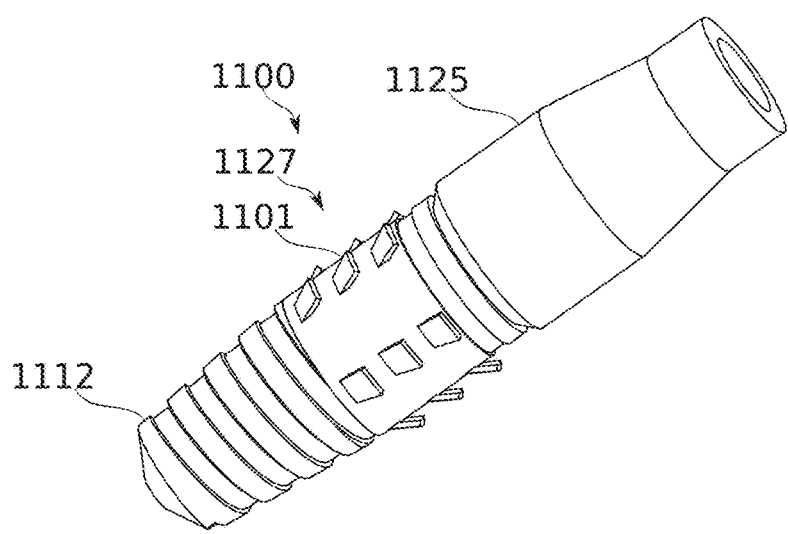
Figures 12A, 12B, 12C:
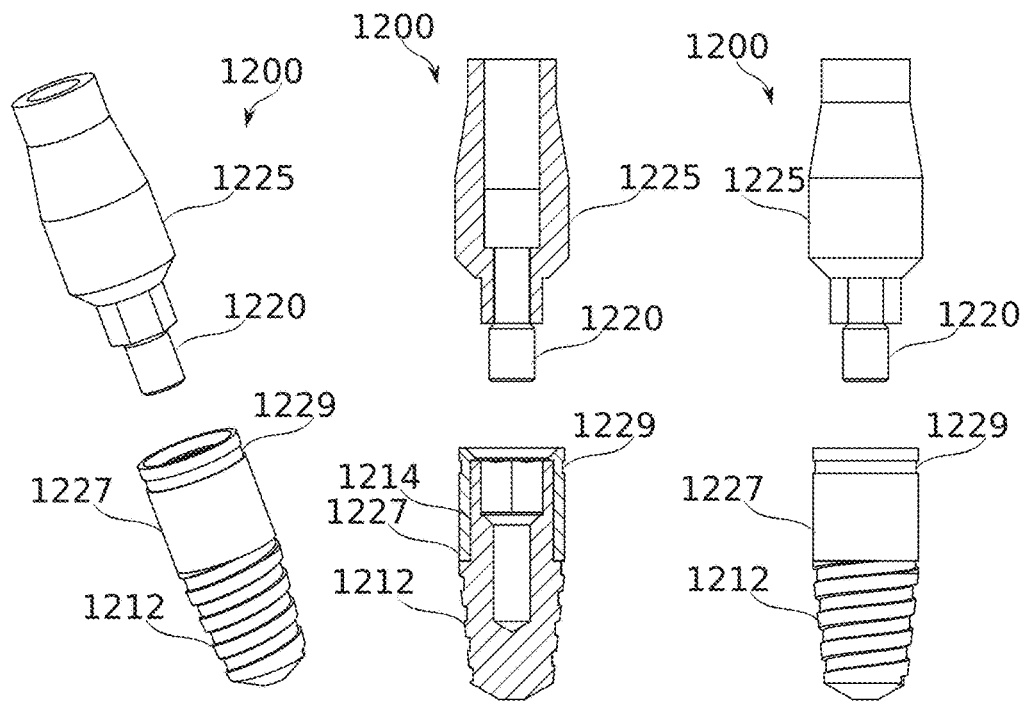
FIGS. 12A-12F schematically illustrate assembled and disassembled perspective, sectional, and facing views of an implant having a single removable insert, according to some exemplary embodiments of the invention.
Figures 12D, 12E, 12F:
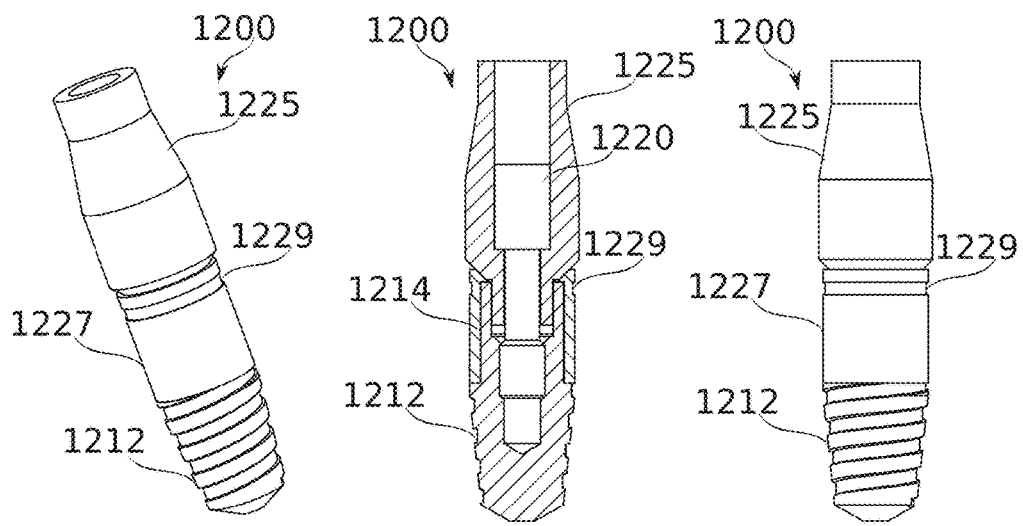

Reference is now made to FIGS. 11A-11C, which schematically illustrate an implant 1100 provided with a removable element sleeve 1127 comprising outward pressing elements 1101, according to some exemplary embodiments of the invention.

Implant 1100 illustrates a more particular embodiment of the concept of FIG. 9B, described hereinabove, for providing additional anchoring support to the implant and/or removable element by contact with bone. In some embodiments, a removable element 1127 comprises a plurality of outward pressing element 1101. In some embodiments, the outward pressing elements are cut from the removable element 1127, in the manner of material punched from a sleeve. In some embodiments, the pressing regions are attached to an intact sleeve body.

Otherwise, the implant 1100 comprises major portions of the implant assembly described in previous embodiments; for example, anchoring base 1112, shaft 1114, and abutment 1125.

Reference is now made to FIGS. 13A-13J, which schematically illustrate removal and/or replacement by a jacketing tool 1300 of a sleeve removable element 1327A, 1327B, 1327C on an implant 1301, 1302, according to some exemplary embodiments of the invention.

In some embodiments, a jacketing tool 1300 is provided for use in extraction and/or replacement of a removable element. In some embodiments, the jacketing tool 1300 comprises two separately moving elements 1303, 1305, which slide over one another. Optionally, for example as shown in FIGS. 13A-13B, element 1303 attaches to implant 1301, for example, by screwing into a receiving hole (the receiving hole may be also used for an abutment screw, or, optionally, is a separately threaded region of the implant). Attachment to the removable element is made, for example, by a ring 1331 at an inset region 1329, or by and at another tooling shape on and/or the jacketing tool 1300, and the removable element 1327A to be removed.

At FIGS. 13C-13D, the removable element 1327A has been removed. The tool 1300 is then detached. FIGS. 13E-13H show the same process in reverse. An removable element 1327B is shown fitted to the tool in FIGS. 13E-13F. In FIGS. 13G-13H, tool is pressed onto the removable element, and the removable element 1327B left behind upon removal of the tool. Optionally, a mechanism is provided to ensure that the removable element 1327B is properly released, rather than pulled off again—for example, in some embodiments, rotation of the tool disengages tool a removable element. Alternatively, the tool is worked off by torquing from side to side, or another method.

Figures 13I, 13J:
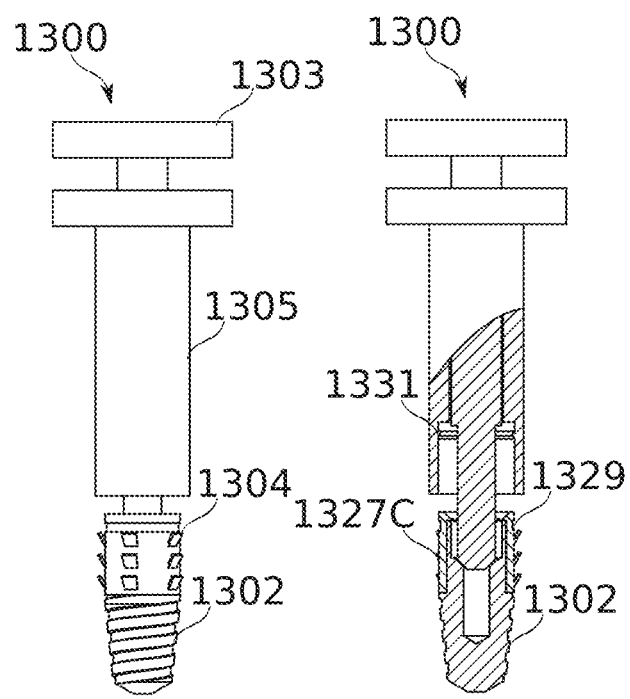

FIGS. 13I-13J illustrate the use of tool 1300 for interacting with an implant 1302 having a sleeve 1327C formed with externally pressing members 1304, such as the implant shown in FIGS. 11A-11C, hereinabove.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A dental implant having an outer surface renewable while the dental implant remains in place, the dental implant comprising:
   an implant body,
   wherein the implant body extends between a proximal end comprising an abutment attachment region, and a distal end including a screw thread for anchoring in a dental socket of a jawbone, and
   wherein the proximal end of the implant body is smaller in diameter than an outer diameter of the distal end to an extent sized for receiving a single thin-walled removable sleeve element; and
   the thin-walled removable sleeve element; fitted around the circumference of the proximal end;
   wherein:
   the removable sleeve element comprises a receiving bore, configured to match the circumference of the proximal end, such that the removable sleeve element is configured to be removed from the circumference of the proximal end, thereby exposing a surface underneath to become a new outer surface,
   a friction fit between an inner surface of the removable sleeve element and the proximal end of the implant body holds the removable sleeve element in a fixed location along a longitudinal axis of the implant, and
   a ratio of thicknesses of the wall of the removable element and of the proximal end of the implant body is about 1:10 or a smaller ratio, such that the implant body maintains an approximately functionally equivalent implant shape to the complete dental implant upon removal of the removable sleeve element, including sufficient width for osseointegration and strength sufficient for functional support of a prosthetic device including acting as an anchoring base for an abutment attached to the abutment attachment region, wherein the friction between the inner surface of the sleeve and the outer surface of the proximal end of the implant body is developed by a partial collapse of the inner surface of the sleeve onto the outer surface of the proximal end of the implant body.

2. The dental implant of claim 1, wherein the exposed surface of the proximal end is prepared to promote osseointegration.

3. The dental implant of claim 2, wherein the exposed surface of the proximal end has a surface geometry which promotes osseointegration.

4. The dental implant of claim 2, wherein the exposed surface of the proximal end has a coating which promotes osseointegration.

5. The dental implant of claim 2, wherein an outer surface of the removable sleeve element is prepared to promote osseointegration.

6. The dental implant of claim 1, wherein the friction fit resists movement in response to a displacement force of at least 10 Newtons applied to the removable element.

7. The dental implant of claim 1, wherein the removable sleeve element extends along at least 30% of the implant body.

8. The dental implant of claim 1, wherein the removable sleeve element extends along at least 5 mm of the implant body.

9. The dental implant of claim 1, wherein the removable sleeve element wall thickness is within the range of 200-400 µm.

10. The dental implant of claim 1, wherein the removable sleeve element extends distally from the abutment attachment region.

11. The dental implant of claim 1, wherein the removable sleeve element extends proximally from the screw thread.

12. The dental implant of claim 1, wherein the friction fit comprises a circumferential seal which prevents bacterial invasion.

13. The dental implant of claim 1, wherein the proximal end including the abutment attachment region and the distal end including the screw thread are integrally formed as a monoblock.

14. The dental implant of claim 1, wherein the removable sleeve element wall thickness is less than 250 µm.

15. The dental implant of claim 1, wherein the removable sleeve element comprises a removable element radial center, and wherein the receiving bore is offset from the removable element radial center.

16. The dental implant of claim 1, further comprising the abutment.

17. The dental implant of claim 5, wherein the outer surface of the removable sleeve element is provided with an external surface treatment selected from the group of sandblast, sandblast large grit acid etch, titanium porous oxide, anodic oxidation, acid etching, CaP coating, titanium plasma spray, hydroxyapatite, resorbable blast media, wet shot blasting, aluminium oxide, recrystallized hydroxyapatite, beta tri-calcium phosphate coating, TiO2 blast, fluoride hydrofluoric acid, hydroxyl apatite blast, sandblast large grit acid edge and NaCl solution, soluble blast media, glow discharge, titanium bead sintering, titanium-zirconium ceramic coating, titanium-niobium ceramic coating, TiO2 coated, laser treatment, anodic spark deposition, plasma rich growth factors, titanium nitride coating, laser sintering, conditioning/hydroxylation, and CaP coated.

18. The dental implant of claim 1 wherein:
   the removable sleeve element wall is flexible to laterally expand upon receiving longitudinal compressive force, the lateral expansion remaining upon removal of the longitudinal compressive force.

19. The dental implant of claim 1, wherein the partial collapse comprises buckling due to the exertion of longitudinal compression on the sleeve.

20. The dental implant of claim 1, wherein the partial collapse comprises radial shrinkage due to the exertion of at least one of: torsion or longitudinal tension, on the sleeve.

* * * * *